US012718365B2

(12) United States Patent
Hu et al.

(10) Patent No.: US 12,718,365 B2
(45) Date of Patent: Aug. 25, 2026

(54) INTELLIGENT PLAN OPTIMIZATION METHOD AND SYSTEM

(71) Applicant: SUPERACCURACY SCIENCE & TECHNOLOGY CO., LTD., Nanjing (CN)

(72) Inventors: Liqin Hu, Nanjing (CN); Dong Wang, Nanjing (CN); Yang Yuan, Nanjing (CN); Jing Jia, Nanjing (CN)

(73) Assignee: SUPERACCURACY SCIENCE & TECHNOLOGY CO., LTD., Nanjing (CN)

( * ) Notice: Subject to any disclaimer, the term of this patent is extended or adjusted under 35 U.S.C. 154(b) by 307 days.

(21) Appl. No.: 18/633,595

(22) Filed: Apr. 12, 2024

(65) Prior Publication Data

US 2025/0029238 A1 Jan. 23, 2025

(30) Foreign Application Priority Data

Jul. 17, 2023 (CN) ......................... 202310874300.1

(51) Int. Cl.
*G06T 7/00* (2017.01)
*G06T 3/40* (2024.01)
(Continued)

(52) U.S. Cl.
CPC .............. *G06T 7/0012* (2013.01); *G06T 3/40* (2013.01); *G06T 5/50* (2013.01); *G06T 15/00* (2013.01);
(Continued)

(58) Field of Classification Search
CPC .... G06V 10/46; G06V 10/764; G06V 10/766; G06V 10/77; G06V 10/82;
(Continued)

(56) References Cited

U.S. PATENT DOCUMENTS 10,525,283 B2 * 1/2020 MacDonald ......... A61N 5/1047
11,557,390 B2 * 1/2023 Hibbard ............... A61N 5/1031
(Continued)

FOREIGN PATENT DOCUMENTS

CN 107441637 B 6/2019
CN 113096766 A 7/2021
(Continued)

OTHER PUBLICATIONS

Notification to Grant Patent Right for Invention in Chinese Application No. 202310874300.1 mailed on Jan. 12, 2026, 2 pages.
(Continued)

*Primary Examiner* — Atiba O Fitzpatrick
*Assistant Examiner* — Rebecca Colette Williams
(74) *Attorney, Agent, or Firm* — PORUS IP LLC

(57) ABSTRACT

A method and system for intelligent plan optimization. The method may include: obtaining a sample scan image, one or more sample contour images, and sample dose data by resampling a scan image, a contour image, and dose data at a same resolution; obtaining a weighted image by the one or more sample contour images; obtaining a sample weighted image by performing a dimensionality reduction on the weighted image; obtaining a trained regression model by performing a regression training on an initial regression model based on the sample scan image, the contour image of the sample target region, the sample weighted image, and the sample dose data corresponding to the sample scan image; and obtaining a dose prediction result by inputting a to-be-tested scan image, a to-be-tested contour image of the target region, and a to-be-tested weighted image after the dimensionality reduction into the trained regression model.

15 Claims, 6 Drawing Sheets

(51) Int. Cl.

| | |
|---|---|
| ***G06T 5/50*** | (2006.01) |
| ***G06T 15/00*** | (2011.01) |
| ***G06V 10/46*** | (2022.01) |
| ***G06V 10/764*** | (2022.01) |
| ***G16H 20/40*** | (2018.01) |

(52) U.S. Cl.
CPC ............ *G06V 10/46* (2022.01); *G06V 10/764* (2022.01); *G16H 20/40* (2018.01); *G06T 2207/20132* (2013.01); *G06T 2207/20221* (2013.01); *G06T 2207/30096* (2013.01)

(58) Field of Classification Search
CPC ..... G06V 2201/03; G06T 7/0012; G06T 3/40; G06T 5/50; G06T 15/00; G06T 2207/20132; G06T 2207/20221; G06T 2207/30096; G16H 20/40; G16H 30/40; A61N 5/103; A61N 5/1031; G06N 3/0464; G06N 3/08
See application file for complete search history.

(56) References Cited

U.S. PATENT DOCUMENTS

| | | | |
|---|---|---|---|
| 2019/0192880 | A1 | 6/2019 | Hibbard |
| 2023/0043026 | A1 | 2/2023 | Duan et al. |

FOREIGN PATENT DOCUMENTS

| | | | |
|---|---|---|---|
| CN | 114155934 | A | 3/2022 |
| CN | 114926487 | A | 8/2022 |
| CN | 115620870 | A | 1/2023 |
| CN | 116030938 | A | 4/2023 |
| CN | 110197709 | B | 6/2023 |

OTHER PUBLICATIONS

First Office Action in Chinese Application No. 202310874300.1 mailed on Jul. 15, 2025, 12 pages.

* cited by examiner

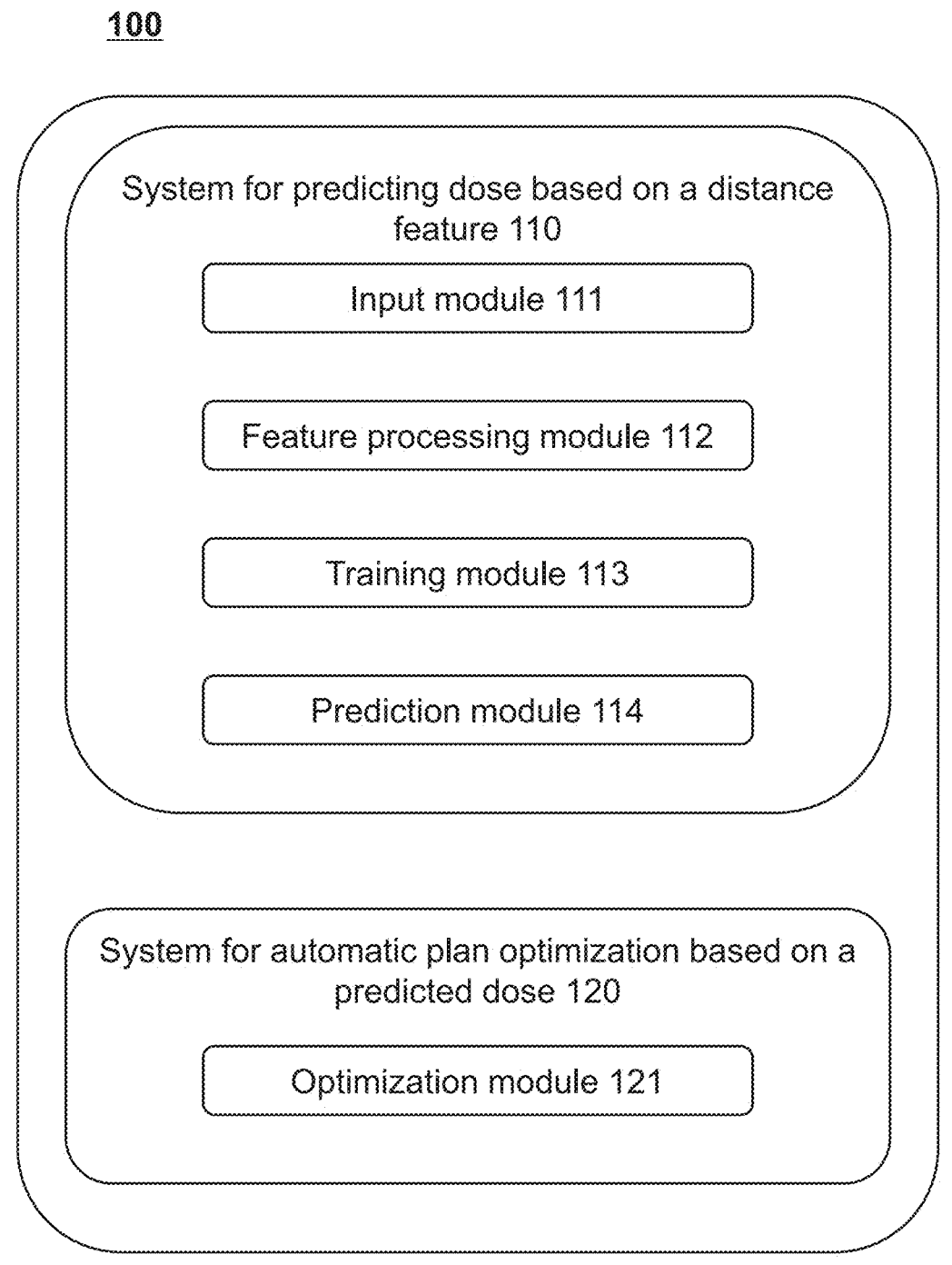

100
System for predicting dose based on a distance feature 110
Input module 111
Feature processing module 112
Training module 113
Prediction module 114
System for automatic plan optimization based on a predicted dose 120
Optimization module 121

INTELLIGENT PLAN OPTIMIZATION METHOD AND SYSTEM

CROSS REFERENCE TO RELATED APPLICATIONS

This application claims priority to Chinese Patent t application No. 202310874300.1 filed on Jul. 17, 2023, the entire contents of which are incorporated herein by reference

TECHNICAL FIELD

The present disclosure relates to the technical field of radiation therapy, and in particular, to a method and a system for intelligent plan optimization.

BACKGROUND

In an intensity-modulated radiation therapy, physicists have to repeatedly adjust parameters of a target region and an organ at risk (OAR) to improve an optimization result to meet a clinical criteria. In the prior art, in order to solve a problem of predicting a three-dimensional (3D) distribution of dose, a method for predicting the dose distribution in an intensity-modulated radiation therapy based on deep learning (CN114155934A) is proposed. In the method, the 3D dose distribution is predicted by constructing a distance image together with a computerized tomography (CT) image, a contour image, etc., as features. However, the method does not consider a combined relationship between the distance and the contour, which causes an input feature to have excessively great dimensions.

Therefore, a system for intelligent plan optimization is provided, which helps to improve an accuracy of the prediction and an efficiency of the optimization of a radiotherapy plan.

SUMMARY

One or more embodiments of the present disclosure provide a method for intelligent plan optimization. The method may include: obtaining a scan image, one or more contour images, and dose data of a case. The one or more contour images may include at least one contour image of a target region (or referred to as a target region contour image) and at least one contour image of an organ at risk (OAR); obtaining a sample scan image, one or more sample contour images, and sample dose data by resampling the scan image, the one or more contour images, and the dose data a same resolution, the one or more sample contour images including at least one contour image of a sample target region (or referred to as sample target region contour image) and at least one image of a sample OAR (or referred to as a sample OAR image); obtaining, based on the one or more sample contour images, contour coordinates of the target region, and calculating a shortest distance from each voxel coordinate of the OAR to the contour coordinates of the target region to obtain a distance image of the OAR; obtaining a weighted image by combining the distance image and the image of the sample OAR; obtaining a sample weighted image by performing a dimensionality reduction on the weighted image; obtaining a trained regression model by performing a regression training on an initial regression model based on the sample scan image, the contour image of the sample target region, the sample weighted image, and the sample dose data corresponding to the sample scan image, the regression model being a machine learning model; and obtaining a dose prediction result by inputting a to-be-tested scan image, a to-be-tested contour image of the target region, and a to-be-tested weighted image after the dimensionality reduction into the trained regression model.

One or more embodiments of the present disclosure provide a system for intelligent plan optimization. The system may include: an input module configured to obtain a scan image, one or more contour images, and dose data of a case. The one or more contour images may include at least one contour image of a target region and at least one contour image of the OAR. The system may include a feature processing module configured to obtain a sample scan image, one or more sample contour images, and sample dose data by resampling the scan image, the one or more contour images, and the dose data at a same resolution, the one or more sample contour images including at least one contour image of a sample target region and at least one image of a sample OAR; obtain, based on the one or more sample contour images, contour coordinates of the target region, and calculate a shortest distance from voxel coordinates of the OAR to the contour coordinates of the target region to obtain a distance image of the OAR; obtain a weighted image by combining the distance image and the image of the sample OAR; and obtain a sample weighted image by performing a dimensionality reduction on the weighted image.

The system for predicting the dose based on the distance feature may further include a training module configured to obtain a trained regression model by performing a regression training on an initial regression model based on the sample scan image, the contour image of the sample target region, the sample weighted image and the sample dose data corresponding to the sample scan image, the regression model being a machine learning model; a prediction module configured to obtain a dose prediction result by inputting a to-be-tested scan image, a to-be-tested contour image of the target region, and a to-be-tested weighted image after the dimensionality reduction into the trained regression model.

One or more embodiments of the present disclosure provide a system for automatic plan optimization based on a predicted dose including an optimization module. The optimization module may be configured to: calculate, based on a dose prediction result, a target function for a target region and an OAR to complete an automatic plan optimization, the target function including: $F_{obj}=\Sigma_j\alpha_j*(d_j-p_j)^2$; where $d_j$ denotes a calculated dose at the jth point, $p_j$ denotes a dose value at the jth point in the dose prediction result, and $\alpha_j$ denotes a constraint penalty factor; obtain the calculated dose $d_j$ for each point in the dose prediction result by calculating a minimal value of the target function $F_{obj}$; and obtain a target radiotherapy plan by optimizing an original radiotherapy plan based on the calculated dose $d_j$.

BRIEF DESCRIPTION OF THE DRAWINGS

This disclosure will be further illustrated by way of exemplary embodiments, which will be described in detail by means of the accompanying drawings. These embodiments are not limiting, and in these embodiments, the same counting denotes the same structure, wherein:

FIG. 1 is a schematic diagram illustrating a structure of a system for intelligent plan optimization according to some embodiments of the present disclosure;

DETAILED DESCRIPTION

Figure 2:
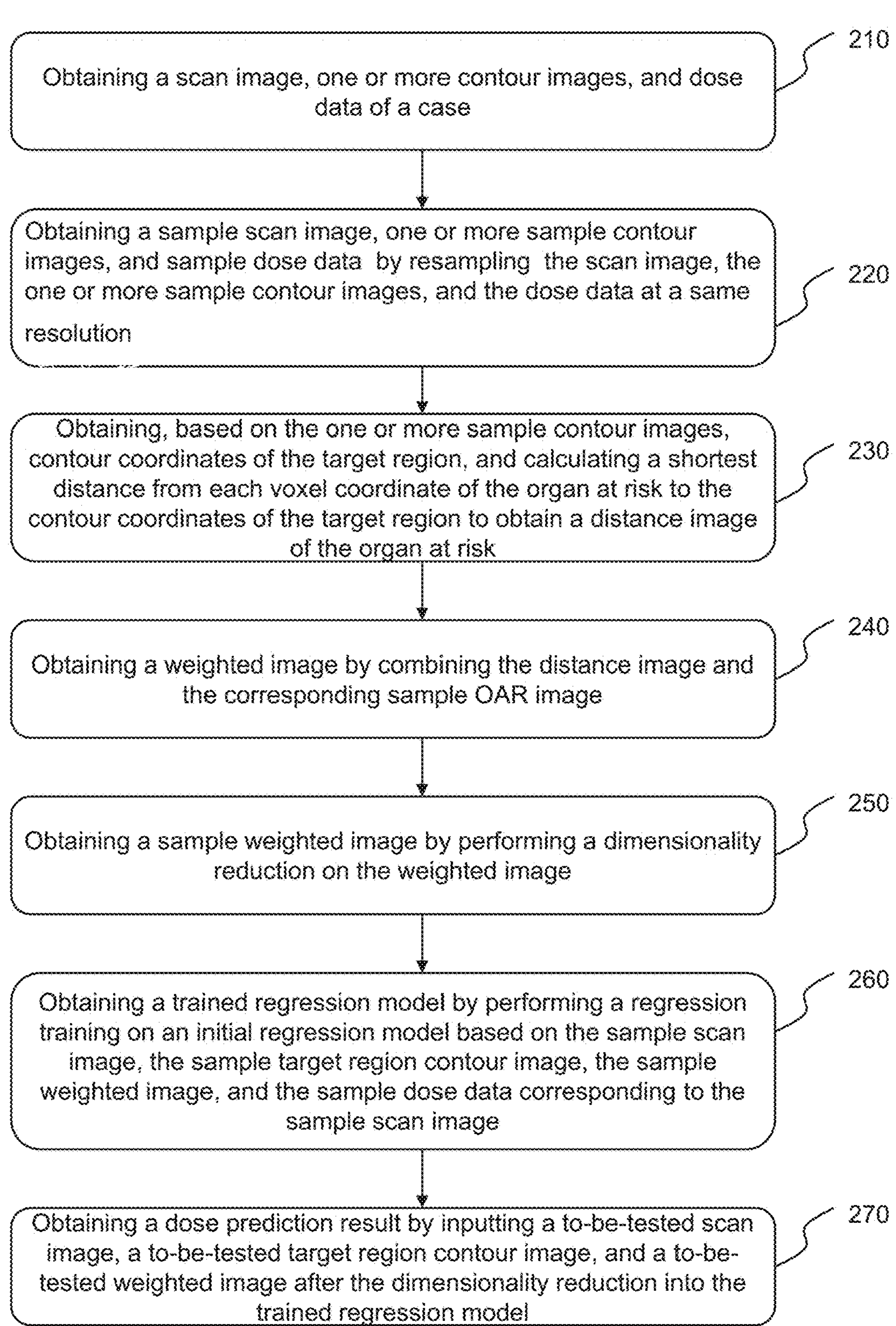
FIG. 2 is a flowchart illustrating an exemplary method for intelligent plan optimization according to some embodiments of the present disclosure.

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for those skilled in the art to apply the present disclosure to other similar scenarios according to these drawings without creative labor. Unless obviously obtained from the context or the context illustrates otherwise, the same numeral in the drawings refers to the same structure or operation.

It should be understood that as used herein, the terms "system," "device," "unit," and/or "module" as used herein is a way to distinguish between different components, elements, parts, sections, or assemblies at different levels. However, the words may be replaced by other expressions if other words accomplish the same purpose.

As shown in the present disclosure and in the claims, unless the context clearly suggests an exception, the words "a," "an," "one," and/or "the" do not refer specifically to the singular, but may also include the plural. Generally, the terms "including" and "comprising" suggest only the inclusion of clearly identified steps and elements that do not constitute an exclusive list, and the method or device may also include other steps or elements.

Flowcharts are used in the present disclosure to illustrate operations performed by a system according to embodiments of the present disclosure. It should be appreciated that the preceding or following operations are not necessarily performed in an exact sequence. Instead, steps may be processed in reverse order or simultaneously. Also, it is possible to add other operations to these processes or remove a step or steps from them.

An intensity-modulated radiation therapy (IMRT) is a kind of three-dimensional (3D) conformal radiotherapy, which requires an intensity of a beam in a radiation field to be adjusted according to certain requirements. The IMRT may include that: under a condition that shapes of the radiation fields and a target region are consistent everywhere, the beam intensity may be adjusted according to a 3D shape of the target region and a specific anatomical relationship between vital organs and the target region. A dose distribution within a single radiation field may be uneven, but the dose distribution in a whole volume of the target region may be more uniform than a traditional 3D conformal radiation therapy. The radiation therapy plan is designed to ensure that the target region receives required dose coverage and intensity while minimizing an exposure to surrounding normal tissue. During the planning process, physicists have to repeatedly adjust parameters of a target region and an organ at risk (OAR), until the dose distribution generated by the therapy plan system meets a clinical standard, but a quality of the treatment plan may also vary depending on an experience level, an effort level, and other differences of the physicists.

To solve a problem of parameter adjustment and optimization in the treatment planning system, CN114155934A proposes a method for predicting a dose in a tumor intensity-modulated radiation therapy based on deep learning, which predicts the dose distribution of the target region and organs at risk by an encoder that mixes convolution and Transformer. However, a dimensionality of an input feature of the method is too large, which is easy to cause model overfitting; and with an increase of the dimensionality of the input feature, data becomes very sparse, which makes it difficult for the model to learn useful information from the input.

In view of the foregoing, some embodiments of the present disclosure provide a system for intelligent plan optimization for obtaining a weighted image by combining a distance image and a corresponding sample OAR image. In this way, a spatial position and shape information of the target region as well as an anatomical structure and functional information of the OAR may be provided, which facilitates a more comprehensive and accurate prediction of the dose by fusing information from two different sources. Moreover, by restoring the dimensionality of the weighted image, the dimensionality of the input feature may be reduced while retaining as much useful information as possible, so as to improve the accuracy and stability of a regression model.

FIG. 1 is a schematic diagram illustrating a structure of a system for intelligent plan optimization according to some embodiments of the present disclosure.

In some embodiments, a system for intelligent plan optimization 100 may be configured to provide a radiation therapy (e.g., at least one of a stereotactic radiosurgery or a precision radiation therapy) for a target region (e.g., a lesion, a tumor) of an object (e.g., a patient), as well as for any other position of the radiation therapy. In some embodiments, the system for intelligent plan optimization 100 may include a treatment planning system, an image-guided radiation therapy system, etc. In some embodiments, the system for intelligent plan optimization 100 may perform an image-guided radiation therapy.

For example, the system for intelligent plan optimization 100 may use X-ray imaging to monitor the target region (e.g., the tumor, the lesion, etc.) for treatment within the object (e.g., the patient). In this case, the system for intelligent plan optimization 100 may include a treatment device (also referred to as a treatment assembly) and an imaging device (also referred to as an imaging assembly).

The treatment device may be configured to radiate a treatment beam to the target region for radiation therapy of that target region. The imaging device (e.g., a positron emission tomography (PET) detector, a computerized tomography (CT) imaging assembly) may be configured to perform imaging (e.g., two-dimensional (2D) imaging, 3D imaging, or four-dimensional (4D) imaging) the target region and/or a normal tissue surrounding the target region before, after, or during the radiation therapy. In this case, an anatomical structure of the target region (e.g., a target section, an OAR) and movement or deformation thereof may be detected, and at least one of the position of the patient or the treatment beam may be adjusted to radiate a radiation dose more accurately to the target region.

As shown in FIG. 1, the system for intelligent plan optimization 100 may include a system for predicting a dose based on a distance feature 110 and a system for automatic plan optimization based on a predicted dose 120. The system for predicting the dose based on the distance feature 110 may include: an input module 111, a feature processing module 112, a training module 113, a prediction module 114, etc.

The input module 111 may be configured to obtain a scan image, one or more contour images, and dose data of a case. The one or more contour images may include at least one target region contour image (or referred to as a contour image of a target region) and at least one OAR contour image (or referred to as a contour image of an OAR).

The feature processing module 112 may be configured to obtain a sample scan image, one or more sample contour images, and sample dose data by resampling the scan image, the one or more contour images, and the dose data at a same resolution, the one or more sample contour images including at least one contour image of a sample target region and at least one image of a sample OAR. The feature processing module 112 may further be configured to obtain, based on the one or more sample contour images, contour coordinates of the target region, and calculate a shortest distance from voxel coordinates of the OAR to the contour coordinates of the target region to obtain a distance image of the OAR; obtain a weighted image by combining the distance image and the image of the sample OAR; and obtain a sample weighted image by performing a dimensionality reduction on the weighted image.

The training module 113 may be configured to obtain a trained regression model by performing a regression training on an initial regression model based on the sample scan image, the contour image of the sample target region, the sample weighted image and the sample dose data corresponding to the sample scan image. The regression model may be a machine learning model.

The prediction module 114 may be configured to obtain a dose prediction result by inputting a to-be-tested scan image, a to-be-tested contour image of the target region, and a to-be-tested weighted image after the dimensionality reduction into the trained regression model.

In some embodiments, the feature processing module 112 may further be configured to obtain a one-dimensional vector and form a multi-dimensional matrix by expanding the weighted image; obtain a plurality of principal components by performing a dimensionality reduction on the multi-dimensional matrix using principal component analysis; and screen, based on the plurality of the principal components, a target principal component that satisfies a preset condition according to a variance; and obtain the sample weighted image.

In some embodiments, the feature processing module 112 may further be configured to: obtain an initial scan image by resampling the scan image; insert the dose data by means of interpolation to a position at which a scanned slice is located in a preset direction; obtain initial dose data by resampling the interpolated dose data and filling resampled dose data to a size of the scan image; obtain an initial contour image by resampling the contour image; and obtain the sample scan image, the sample contour image, and the sample dose data by cropping the initial scan image, the initial dose data, and the initial contour image to a preset size.

In some embodiments, the shortest distance from the voxel coordinates of the OAR to the contour coordinates of the target region may be determined by the following equation:

$$D=\left(\min_{t\in V_{OARS},s\in\Pi_{PTV}} d(t_{i,j,k},s)_{i,j,k}\right)_{l\times h\times w}$$

where, D denotes the shortest distance, $V_{OARS}$ and $\Pi_{PTV}$ respectively denotes a set of 3D coordinates of the OAR and a set of 3D coordinates of a contour of the target region (or referred to as a target region contour), $t_{i,j,k}$ denotes coordinates of a voxel at (i, j, k) in the OAR, s denotes coordinates of a point on the target region contour, d denotes a distance function, and (l, h, w) denotes a count of slices, a length, and a width of the distance image, respectively.

In some embodiments, the feature processing module 112 may further be configured to: obtain a reciprocal image by taking a reciprocal of the distance image; and obtain the weighted image by inter-element multiplication based on the reciprocal image and the corresponding sample contour image, the inter-element multiplication being performed by the following equation:

$$C'=\left(c_{i,j,k}*d'_{i,j,k}\right)_{l\times h\times w};$$

$$c_{i,j,k}=\begin{cases}1, & c_{i,j,k}\in R_{OAR}\\ 0, & \text{others}\end{cases};$$

$$d'_{i,j,k}=\begin{cases}d_{i,j,k}^{-1}, & d_{i,j,k}\neq 0\\ N, & d_{i,j,k}=0\end{cases};$$

where, C' denotes the weighted image, $c_{i,j,k}$ denotes a mask value of the voxel at (i, j, k) in the sample OAR image, $R_{OAR}$ denotes a set of 3D coordinates of a contoured region with a mask value of 1, d' denotes the reciprocal image, $d_{i,j,k}$ denotes a shortest distance value from the voxel at (i, j, k) in the distance image, and N denotes a constant.

In some embodiments, the system for intelligent plan optimization 100 may include a classification module (not shown in the figure). The classification module may be configured to: determine, based on the sample dose data, a classification result of each voxel through a binary classification model, and screen a dose region as input data for the regression training.

In some embodiments, the regression model may include a down-sampling operation and an up-sampling operation. The down-sampling operation may include at least one of a convolution operation, a normalization operation, and an activation operation, and the up-sampling operation may at least include a splicing operation. The training module 113 may further be configured to: input the sample scan image, the sample target region contour image, and the sample weighted image into the initial regression model, construct a loss function through the dose data corresponding to the sample scan image and the dose prediction result output form an initial determination model, iteratively update parameters of the initial regression model based on the loss function through an optimizer, and complete the model training when a termination condition is satisfied to obtain the trained regression model.

In some embodiments, the training module 113 may further be configured to: train, based on the training sample, a discriminant network and the regression model by means of a generative adversarial network.

In some embodiments, the training module 113 may further be configured to: determine, based on a tumor type, different training samples and the corresponding labels; and alternately train the regression model based on training samples of different scale sizes. The different training samples may have different learning rates during a training process, and the learning rates may be adjusted based on a training sample feature.

In some embodiments, the learning rates may include the learning rates of a plurality of training stages, the learning rate of each of the plurality of training stages being updated based on a training loss of the training stage.

In some embodiments, the resolution may be determined based on a tumor type, a tumor position, and a tumor size corresponding to the to-be-tested scan image.

In some embodiments, the feature processing module 112 may further be configured to determine the resolution by: determining a resolution interval based on the tumor type, the tumor position, and the tumor size; generating a plurality of candidate resolutions based on the resolution interval; and determining a target resolution based on the plurality of candidate resolutions.

In some embodiments, the feature processing module 112 may further be configured to: for each of the candidate resolution, obtain a corresponding candidate scan image, a candidate target region contour image, and a candidate weighted image by resampling based on the candidate resolution; determine, based on the candidate scan image, the candidate target region contour image, and a downscaled candidate weighted image, a candidate dose prediction result corresponding to the candidate resolution by a regression model; determine an optimized resolution based on the candidate resolution and the candidate dose prediction result corresponding to the candidate resolution; and determine the target resolution based on the optimized resolution.

In some embodiments, the system for automatic plan optimization based on a predicted dose 120 may include an optimization module 121. The optimization module 121 may be configured to: calculate, based on a dose prediction result, a target function for a target region and an OAR to complete an automatic plan optimization. The target function may include:

$$F_{obj} = \sum_{j} \alpha_j * (d_j - p_j)^2$$

where, $d_j$ denotes a calculated dose at the jth point, $p_j$ denotes a dose value at the jth point in the dose prediction result, and $\alpha_j$ denotes a constraint penalty factor. The calculated dose $d_j$ for each point in the dose prediction result may be obtained by calculating a minimal value of the target function $F_{obj}$; and a target radiotherapy plan may be obtained by optimizing an original radiotherapy plan based on the calculated dose $d_j$.

In some embodiments, the system for intelligent plan optimization 100 may include a network and/or other components that connect the system to external resources. The processor may access data and/or information related to the system for intelligent plan optimization 100 via the network.

In some embodiments, the system for intelligent plan optimization 100 may further include a terminal device. The terminal device refers to one or more terminal devices used by user, and the processor may be integrated into the terminal device.

In some embodiments, the system for intelligent plan optimization 100 may also include a storage module for storing data, instructions, and/or any other information. For example, the storage module may store the scan image, the contour image, and the dose data of a case, etc.

In some embodiments, the storage module may include random access memory (RAM), read-only memory (ROM), etc. or any combination thereof. In some embodiments, the storage module may be integrated or included in one or more other components (e.g., the processor, the terminal device, etc.) of the system for intelligent plan optimization 100.

For more contents of the input module 111, the feature processing module 112, the training module 113, and the prediction module 114, please refer to the related descriptions as follow.

In some embodiments, the input module 111, the feature processing module 112, the training module 113, and the prediction module 114 may be integrated into a processor, and a process 200 in FIG. 2 below may be performed by the processor.

It may be noted that the above description of the system for intelligent plan optimization 100 and the modules thereof are provided only for descriptive convenience, and do not limit the present disclosure to the scope of the cited embodiments. It may be understood that for those skilled in the art, after understanding the principle of the system, it may be possible to arbitrarily combine individual modules or form subsystems that are connected to other modules without departing from this principle. For example, the individual modules may share a common storage module, and the individual modules may each have their own storage module. Such changes are within the scope of protection of the present disclosure.

FIG. 2 is a flowchart illustrating an exemplary method for intelligent plan optimization according to some embodiments of the present disclosure. In some embodiments, the process 200 may be performed by a processor of the system for intelligent plan optimization. As shown in FIG. 2, the process 200 may include the following steps.

Step 210, obtaining a scan image, one or more contour images, and dose data of a case.

The case refers to an object for which a dose prediction is required. The case may include a biological or non-biological object. In some embodiments, the object may include a patient, an artificial object, etc. In some embodiments, the object may include a particular portion of the patient, an organ, and/or a tissue. For example, the object may include a head, a brain, a neck, a body, a shoulder, an arm, a chest, a heart, a stomach, a blood vessel, a soft tissue, a knee, a foot, etc., or any combination thereof. The scan image refers to an image configured to reflect an internal organization of the object. In some embodiments, the scan image may reflect structural and positional information of a target region and an OAR region of the object.

In some embodiments, the scan image may be data provided by a physician. In some embodiments, the processor may obtain the scan image of the object by reading from a storage device, a database (e.g., a picture archiving and communication system (PACS)), calling a data interface, etc.

In some embodiments, the scan image may include a 2D image, a 3D image, or a 4D image. In some embodiments, the scan image may include a single modality image, e.g., an ultrasound image, an X-ray image, a CT image, a magnetic resonance imaging (MRI) image, a PET image, a single photon emission computed tomography (SPECT) image, etc. In some embodiments, the scan image may include a multimodal image, e.g., a SPECT-MRI image, a PET-CT image, a SPECT-CT image, a CT-MRI image, etc. The present disclosure does not limit the type of the scan image.

The contour image refers to an image configured to depict or trace an existing image. For example, the contour image may include a contour or path of at least one pre-existing image. The pre-existing image may be an image that refers to the internal organization of the object.

In some embodiments, the contour image may include at least one target region contour image and at least one OAR contour image. The target region contour image refers to an image that includes a contour or path of a target region for radiotherapy. The OAR contour image refers to an image that includes a contour or path of the OAR.

The target region refers to a region of a body of a patient that is irradiated with a certain absorbed dose in the radiation therapy. For example, a lesion region, a tumor region.

The OAR refers to healthy tissue or organ involved in the radiation field during radiation therapy. For example, the OAR may include a count of organs and tissues surrounding the target region.

In some embodiments, the contour image may include an image showing the target region and/or the OAR as manually contoured by the physicist or automatically contoured, such as a planning target volume (PTV) contour image, an OAR contour image, etc.

In some embodiments, the processor may determine the contour images of the target region and the OAR based on various algorithms, templates, or machine learning models, etc. The contour image may include segmenting a boundary of a region of interest in the scan image.

Merely by way of example, the contour image may include a segmentation boundary between the target region contour image and the OAR in the scan image, and/or a boundary between the target region contour image and the OAR and the background region. For example, the contour image of a lower abdomen of the object may include contoured traces of a "tumor," a "femur," a "bladder," and a "rectum" in the medical image of the lower abdomen of the object. In some embodiments, the processor may obtain information about the contour image of a user on the object achieved from a terminal device.

The dose data refers to a radiation dose that is actually distributed to each unit volume of the object. The dose data corresponding to the scan image refers to the radiation dose distributed to each unit volume (e.g., each individual pixel or voxel) in the image of the object.

In some embodiments, the processor may obtain the dose data for the object at various moments through a dose monitoring device (e.g., a real-time dose monitoring system).

Step 220, obtaining a sample scan image, one or more sample contour images, and sample dose data by resampling the scan image, the one or more contour images, and the dose data at a same resolution.

The sample scan image may be a resampled scan image.

The sample contour image may be a resampled contour image.

In some embodiments, the sample contour image may include a sample target region contour image and a sample OAR image. The sample target region contour image may be a resampled target region contour image. The sample OAR image may be a resampled OAR contour image.

The sample dose data may be a resampled dose data.

The resolution refers to a pixel point position or a spacing between the pixel points.

In some embodiments, the processor may obtain the resolution by reading from a storage device, a database, calling a data interface, etc. In some embodiments, the processor may determine the resolution by manual input. The resolution may also be determined based on actual needs.

In some embodiments, the resolution may be determined based on a tumor type, a tumor position and a tumor size corresponding to the scan image. For more contents, please refer to the related description of FIG. 3.

The resampling may be a manner of processing image data. The resampling refers to resampling the image formed by discrete data according to desired pixel point positions or pixel point spacings to form a new image after geometric transformation. A new image with more or fewer pixel points may be obtained after the resampling.

In some embodiments, the resampling may include, but not limited to, a bilinear interpolation algorithm, a nearest neighbor algorithm, a multiple regression interpolation algorithm, a local polynomial interpolation algorithm, etc.

In some embodiments, the processor may resample the scan image, the contour image, and the dose data at the same resolution to obtain the corresponding sample scan image, the sample contour image, and the sample dose data in various manners. For example, the processor may resample the scan image using an interpolation algorithm (e.g., the nearest neighbor interpolation algorithm, a linear interpolation algorithm, a cubic interpolation algorithm, etc.) to match the corresponding resolution. The processor may resample the contour image and the dose data using the same interpolation algorithm as the scan image to ensure that the same resolution as the scan image.

In some embodiments, the processor may obtain an initial scan image by resampling the scan image; insert the dose data by means of interpolation to a position at which a scanned slice is located in a preset direction; obtain initial dose data by resampling the interpolated dose data and filling resampled dose data to a size of the scan image; obtain an initial contour image by resampling the contour image; and obtain the sample scan image, the sample contour image, and the sample dose data by cropping the initial scan image, the initial dose data, and the initial contour image to a preset size.

The initial scan image refers to the resampled scan image to be determined as the sample scan image.

In some embodiments, the processor may resample the scan image in various manners based on an original resolution of the scan image and a target resolution to obtain the initial scan image. The original resolution refers to the resolution of the scan image before resampling. The target resolution refers to the resolution of the scan image desired.

Exemplarily, when the original resolution is greater than the target resolution, and a purpose of the resampling is to reduce the resolution, the purpose may be realized by using a principle of lower-sampling or down-sampling: assuming that a size of the scan image is M*N, and the down-sampling may be performed on the scan image by s times (s is generally a convention count of M and N), i.e., to obtain a resolution image with a size of (M/s)*(N/s), the scan image within an window sized s*s of the original image may be changed into a pixel point whose value is determined based on a count of pixel points of the scan image within the window; after that, determining the initial scan image based on each lower-sampled or down-sampled pixel points. A determination rule may be a maximum or average value of a count of pixel points within the window, etc.

The scanned slices refer to tomographic images of the scan image, which are a series of X-ray images produced by scanning. Each of the scanned slices represents a result of a scan at a different position in the preset direction.

In some embodiments, the scan image may be a series of 2D images (e.g., the scanned slices) stacked in a preset direction (typically a height direction of the patient) to form 3D body data. Each of the scanned slices represents an organizational structure in a plane at a different position in the preset direction.

The insertion refers to obtaining the dose data for the scanned slices at different positions in the preset direction by interpolation.

It may be noted that the dose data is measured at different positions, but not every scanned slice has corresponding sub-dose data, and the missing sub-dose data for each scanned slice may be estimated by an interpolation method. For example, when dose values of the first position and the second position are known, the sub-dose data for the scanned slices between the first position and the second position may be estimated by the interpolation method. The sub-dose data may be configured to indicate a dose distribution at various positions on the scanned slice.

In some embodiments, the processor may select the interpolation method based on the dose data (e.g., whether the dose data is uniformly distributed, whether there is a noise, etc.). Commonly used interpolation methods may include the linear interpolation, the polynomial interpolation, a spline interpolation, the nearest neighbor interpolation, etc.

In some embodiments, during the scanning process of an object, the processor may establish a coordinate system based on the object to describe spatial position and structure of the internal organization of the object. Exemplarily, the processor may establish an XYZ-axis coordinate system based on the object, with an X-axis extending from a left side to a right side of the human body. The X-axis may usually indicate a horizontal direction of the scan image during the scanning (e.g., CT or MRI) process. A Y-axis may extend from a front to a back of the human body, and the Y-axis may usually indicate a vertical direction of the scan image during the scanning process. A Z-axis may extend from a top of a head to a bottom of feet, and in the scanning process, the Z-axis may indicate a direction of scanning (i.e., the preset direction), which is the direction of a layer thickness of the scanned slices. In the scan image, a series of the scanned slices may be stacked together to form a 3D structure of the human body, and the scanned slices may be obtained by scanning along the direction of the Z-axis.

The initial dose data refers to the resampled dose data that is to be determined as the sample dose data.

In some embodiments, the processor may insert the dose data by the interpolation method to a position where the scanned slice is located in the Z-axis direction in various manners. For example, the processor may select a Z-axis position of the scanned slice at which the sub-dose data needs to be inserted; find, among the dose data, the voxel closest to the position of the selected scanned slice; calculate, based on the interpolation method, the selected scanned slices at each position of the voxel, and obtain the sub-dose data corresponding to each of the scanned slices.

In some embodiments, the processor may obtain the initial dose data with the same resolution as the initial scan image by resampling based on the sub-dose data corresponding to the each of the scanned slices.

The initial contour image refers to the contour image after resampling which is to be determined as the sample contour image.

In some embodiments, the processor may resample the contour image to obtain the initial contour image with the same resolution as the initial scan image.

The preset size refers to the preset sizes of the sample scan image, the sample contour image, and the sample dose data. For example, the preset size may include the size of a 3D image, such as 128×128×128 voxels.

In some embodiments, the processor may obtain the preset size based on a manual input or a storage device.

In some embodiments, the processor may crop or fill the sample scan image, the sample contour image, and the sample dose data, to the preset size to obtain the sample scan image, the sample contour image, and the sample dose data. For example, the processor may select, based on a fact that one of the sample scan image, the sample contour image, and the sample dose data, etc., is greater than the preset size, a center region of the corresponding image or data, so as to retain the most important feature; obtain a cropping amount by calculating one-half of the difference between the size of the corresponding image or data minus the preset size, respectively; and crop the respective boundaries of the sample scan image, the sample contour image, and the sample dose data based on the cropping amount. For another example, the processor may resample, based on one of the sample scan image, the sample contour image, the sample dose data, etc. being larger than the preset size, the corresponding image or data to the specified preset size and fill the added pixel positions with zero values (e.g., fill corresponding to black or other specified background color).

In some embodiments of the present disclosure, by resampling and cropping, it may be ensured that all images and dose data have the same resolution and size, so as to facilitate subsequent analysis and computation. In this way, in the subsequent tasks of image alignment, segmentation, analysis, etc., the amount of data that the processor needs to process may be greatly reduced, thus accelerating the computation process.

Step 230, obtaining, based on the one or more sample contour images, contour coordinates of the target region, and calculating a shortest distance from each voxel coordinate of the organ at risk to the contour coordinates of the target region to obtain a distance image of the organ at risk.

The contour coordinates of the target region refers to the 3D spatial coordinates of the region that is to be treated with radiation in radiation therapy and radiation planning. The contour coordinates of the target region may be configured to accurately contour the boundaries of the tumor or a diseased tissue.

The shortest distance refers to a straight-line distance from each voxel (3D pixel) of the OAR to the nearest point on the target region contour in the 3D space.

The distance image refers to an image in which the shortest distance from each of the voxel coordinates of the OAR to the contour coordinates of the target region is taken as the pixel value.

In some embodiments, the processor may determine the distance image based on the sample contour image in various manners. For example, for each voxel of the OAR, the processor may determine the position of the closest point by a search algorithm that determines the distance between the position of the closest point and the corresponding voxel as the shortest distance; construct, based on the shortest distance of each voxel of the OAR, the distance image. Search algorithms may include, but not limited to, an enumeration, a depth-first search, etc.

In some embodiments, the processor may determine the distance image by equation (1):

$$D = \left( \min_{t \in V_{OARS}, s \in \Pi_{PTV}} d(t_{i,j,k}, s)_{i,j,k} \right)_{l \times h \times w}; \quad (1)$$

where D denotes the shortest distance, $V_{OARS}$ and $\Pi_{PTV}$ respectively denotes a set of 3D coordinates of the organ at risk and a set of 3D coordinates of the target region contour, $t_{i,j,k}$ denotes a coordinate of a voxel at (i, j, k) in the organ at risk, s denotes a coordinate of a point on the target region contour, d denotes a distance function, and (l, h, w) denotes a count of slices, a length and a width of the distance image, respectively.

In some embodiments, for each voxel of the OAR, the processor may traverse each point on the target region contour, calculate the distance from the voxel to each point based on the distance function, and filter for the shortest distance. The distance function may include a Euclidean distance, a Manhattan distance, a Chebyshev distance, etc.

In some embodiments of the present disclosure, with the above equation, the accuracy of the shortest distance obtained may be ensured, and an efficiency can be improved when a great count of pixels need to be processed.

Step 240, obtaining a weighted image by combining the distance image and the corresponding sample OAR image.

The weighted image refers to a result of combining the distance image with the corresponding sample OAR image. The weighted image may provide a more comprehensive view or more information, e.g., the weighted image may show positions and relationship of possible diseased regions or OARs.

In some embodiments, the processor may combine the distance image and the corresponding sample OAR image in various manners to obtain the weighted image. For example, the processor may superimpose the distance image and the corresponding sample OAR image, and calculate a weighted average for each pixel. For another example, a first weight may be assigned to the distance image and a second weight may be assigned to the sample OAR image, and the value of each pixel in the weighted image may be a weighted average of the values of the corresponding pixels in both images. The first weight, the second weight may be system default, system preset, etc.

In some embodiments, the processor may obtain a reciprocal image by taking a reciprocal of the distance image; obtain the weighted image by inter-element multiplication based on the reciprocal image and the corresponding sample contour image, and the inter-element multiplication may be carried out by means of Equation (2), Equation (3), and Equation (4):

$$C' = (c_{i,j,k} * d'_{i,j,k})_{l\times h\times w}; \tag{2}$$

$$c_{i,j,k} = \begin{cases} 1, & c_{i,j,k} \in R_{OAR} \\ 0, & \text{others} \end{cases}; \tag{3}$$

$$d'_{i,j,k} = \begin{cases} d^{-1}_{i,j,k}, & d_{i,j,k} \neq 0 \\ N, & d_{i,j,k} = 0 \end{cases}; \tag{4}$$

where, C' denotes the weighted image, $c_{i,j,k}$ denotes a mask value of the voxel at (i, j, k) in the sample organ at risk image, $R_{OAR}$ denotes a set of 3D coordinates of a contoured region with a mask value of 1, d' denotes the reciprocal image, $d_{i,j,k}$ denotes a shortest distance value from the voxel at (i, j, k) in the distance image, and N denotes a constant.

The reciprocal image refers to a new image generated by taking the reciprocal of each voxel value in the distance image. The distance image represents minimum distance from each voxel in the image to a particular point (e.g., the target region contour, etc.), and after taking the reciprocal, the value of each voxel in the reciprocal image may represent the inverse of the shortest distance.

The inter-element multiplication refers to an operation between two matrices or vectors of the same shape. The inter-element multiplication is configured to multiply the reciprocal image by the corresponding element of the corresponding sample contour image.

In some embodiments, when taking the reciprocal, as the inverse is undefined at 0, the processor may perform a special treatment on the 0 value in the distance image to avoid an error in taking the reciprocal. The processor may replace the value of 0 with a non-zero preset value, such as N, or use other methods to handle pixels in the distance image that have a value of 0 to ensure that the entire image is mathematically defined.

In some embodiments of the present disclosure, the distance image may be configured to represent a spatial layout of the various tissues in the object, and the reciprocal image after taking the inverse count may emphasize a variation of a nearby region, e.g., when the distance is relatively small, the reciprocal may be relatively great, which helps to highlight the region that is close to the target region contour in the scene, thus improving the perception and recognition of the nearby region.

Step 250, obtaining a sample weighted image by performing a dimensionality reduction on the weighted image.

The sample weighted image refers to a new image generated after performing the dimensionality reduction on the weighted image.

The dimensionality reduction refers to deleting features in the weighted images and reduce redundant information to facilitate a storage, a transmission or a subsequent image processing.

In some embodiments, the processor may perform the dimensionality reduction to the weighted image to obtain the sample weighted image in various manners. For example, the processor may perform the dimensionality reduction to the weighted image based on an image dimensionality reduction method to obtain the sample weighted image. The image dimensionality reduction method may include, but not limited to, a principal component analysis (PCA), a discrete cosine transform (DCT), etc.

In some embodiments, the processor may obtain a one-dimensional vector and form a multi-dimensional matrix by expanding the weighted image; obtain a plurality of principal components by the dimensionality reduction of the multi-dimensional matrix using principal component analysis; screen, based on the plurality of the principal components, a target principal component that satisfies a preset condition according to a variance; and obtain the sample weighted image by restoring the target principal component after screening to a three-dimensional image.

The one-dimensional vector refers to a one-dimensional array obtained by rearranging all the elements in the weighted image in a certain order.

The expanding refers to the operation of converting the 3D coordinate data of the weighted image into a one-dimensional data structure.

In some embodiments, the processor may take the weighted image, and expand it in a preset order to obtain the one-dimensional vector. The preset order may include a row precedence, a column precedence, a left-to-right, and a top-to-bottom order, etc.

In some embodiments, the processor may expand the weighted image corresponding to a certain OAR to obtain the one-dimensional vector, and by the above means, obtain the one-dimensional vectors corresponding to each of the weighted images of a plurality of organs at risk, and form, based on the plurality of the one-dimensional vectors, the multi-dimensional matrix.

The principal component refers to a vector that capture information about changes in the weighted image.

In some embodiments, the processor may calculate an average of the multi-dimensional matrix, and subtract the average from each element of the multi-dimensional matrix; calculate a covariance matrix of the multi-dimensional matrix after subtracting the average; use a feature value decomposition method to find a feature value and a feature vector of the covariance matrix; and use the feature vector as the principal component. The feature value may be configured to represent a magnitude of the variance of the multi-dimensional matrix in a direction of each of the principal components.

The target principal component refers to the vector that maximize the information about the main changes in the weighted image.

The preset condition refers to a determination condition for selecting the target principal component. For example, the preset condition may include that the variance is the largest, and a cumulative variance contribution exceeds a first proportion. The first proportion may be determined based on an experimentation or experience. Exemplarily, the first proportion may be 95%. The cumulative variance contribution refers to a ratio of a sum of a plurality of feature values to a sum of all the feature values. For more contents on the preset condition, please refer to the related description in FIG. 5.

In some embodiments, the processor may filter the target principal components that satisfy the preset condition according to the variance based on the plurality of the principal components. For example, the processor may sort the feature values from greatest to smallest, select the greatest preset count of feature vectors as the target principal components. The preset count refers to a count such that the cumulative variance contribution satisfies the first proportion.

In some embodiments, the processor may use the target principal components as row vectors, respectively, form a feature vector matrix based on the plurality of row vectors; and perform a linear transformation on the weighted image using the feature vector matrix to obtain the sample weighted image. For example, the feature vector matrix may be multiplied by a matrix of the weighted image to obtain the sample weighted image.

In some embodiments of the present disclosure, high-dimensional weighted image data may require greater calculation resources and time to process. By the dimensionality reduction, a calculation amount may be reduced and a processing speed may be accelerated, which is favorable for real-time processing or great-scale data processing. The dimensionality reduction may improve the performance of a regression model, and by retaining the most important features, the regression model may focus more on learning the key information of the data, thereby improving the prediction accuracy.

Step 260, obtaining a trained regression model by performing a regression training on an initial regression model based on the sample scan image, the sample target region contour image, the sample weighted image, and the sample dose data corresponding to the sample scan image.

The initial regression model refers to the regression model that needs to be trained for regression. In some embodiments, the processing device may obtain the initial regression model from the storage device and/or an external data source via a network. An initial parameter of the initial regression model may be set based on processor defaults.

The regression model refers to an algorithm or model configured to predict a dose prediction result corresponding to the sample scan image.

In some embodiments, the regression model may be a machine learning model. For example, the regression model may be the machine learning model with a custom structure as described below. The regression model may also be the machine learning model of other structures, including one or a combination of a convolutional neural network (CNN), a recurrent neural network (RNN), a deep neural network (DNN), a generative adversarial network (GAN), a 3D-Unet network, a Res-net network, etc.

In some embodiments, inputs to the regression model may include a to-be-tested scan image, a to-be-tested target region contour image, and a to-be-tested weighted image after the dimensionality reduction, and outputs may include the dose prediction result. The to-be-tested scan image refers to the scan image of the dose to be predicted. The to-be-tested contour image refers to the contour image corresponding to the scan image of the dose to be predicted. The to-be-tested contour image may include the to-be-tested target region contour image and a to-be-tested OAR contour image. The to-be-tested sample weighted image refers to an image determined based on the to-be-tested contour image by calculating the shortest distance and the combination, etc., as described above. In some embodiments, the to-be-tested scan image, the to-be-tested contour image, and the to-be-tested sample weighted image, etc. may be resampled images.

In some embodiments, the regression model may be trained in various feasible ways based on a great count of first training samples with first labels. For example, a parameter updating may be performed based on a gradient descent method.

In some embodiments, the first training sample may include a plurality of training samples. The training samples may at least include the sample scan image, the sample target region contour image, and the sample weighted image. The first training sample may be obtained based on historical data.

In some embodiments, the first label may include the sample dose data corresponding to the sample scan image determined based on a gold standard. The first label may be obtained by the processor or manual labeling. The determining the dose data based on the gold standard refers to using a recognized, accurate, and reliable method or technique as a standard of reference for determining or validating the dose data obtained by other methods or techniques.

In some embodiments, when generating the regression model by training, the model parameter may be optimized in various manners to make the regression model generated perform better. For example, the optimization manner such as a gradient descent, a moment optimizer, an Adam optimizer, etc. may be used. Exemplarily, the processor may update, based on the Adam optimizer, the parameters of the regression model by continuously optimizing the loss function until the loss function is minimized.

In some embodiments, the processor may divide the first training sample data into three subsets: a training set, a validation set, and a test set. The training set may be configured to train the initial regression model. A proportion of the training set may be a first ratio. The validation set may be configured to adjust the model parameters and evaluating the performance of the regression model during the training process of the initial regression model. A proportion of the validation set may be a second proportion. The test set may be configured to evaluate the performance of the regression model after the regression model training is completed. A proportion of the test set may be is a third ratio. The first ratio, the second proportion, and the third ratio may be determined based on experimentation or experience. In some embodiments, the first ratio may be greater than the second proportion, and the second proportion may be greater than the third ratio.

In some embodiments, the regression model may include a down-sampling operation and an up-sampling operation.

The down-sampling operation may be configured to reduce a size of an input image (e.g., a length and a width of the image). In some embodiments, a down-sampling layer may be implemented based on manners such as a maximum pooling, an average pooling, etc.

In some embodiments, the down-sampling operation may include at least one of a convolution operation, a normalization operation, and an activation operation.

The convolution operation may be configured to perform a convolution operation on data for feature extraction. In some embodiments, the convolution operation may be implemented based on a convolution kernel. For example, the convolution operation may include performing sliding over the input data based on the convolution kernel (or filter, as it may be called), and weighting and summarizing the data at each position to obtain a new feature image.

In some embodiments, different convolution parameters may correspond to different convolution operations. The convolution parameters may include, but not limited to, a size of the convolution kernel, a filling, a step size, etc. In some embodiments, different convolution parameters may be determined based on experimentation or experience. For example, the convolution kernel size may be 3, the filling may be 1, and the step size may be 1.

The normalization operation may be configured to limit the data to a certain range after processing (by certain algorithm). In some embodiments, the normalization operation may be implemented based on, for example, a batch Normalization and a layer Normalization.

The activation operation refers to a nonlinear transformation of data by activation function. The activation function may include, but not limited to, a Sigmoid, a Tanh, a rectified linear unit, (ReLU), etc.

The up-sampling operation may be configured to increase the size of the input image (e.g., the length and the width of the image). In some embodiments, an up-sampling layer may be implemented based on methods such as a transposed convolution, the bilinear interpolation, etc.

In some embodiments, the up-sampling operation may at least include a splicing operation.

The splicing operation refers to a method of combining a plurality of images into a completely new image according to certain rules. The splicing operation may include splicing by horizontal direction, splicing by vertical direction, splicing by channel direction, etc.

In some embodiments, the network structure of the regression model may present a U-shape.

In some embodiments, the regression model may include a first down-sampling network, a second down-sampling network, a third down-sampling network, a fourth down-sampling network, a fifth up-sampling network, a sixth up-sampling network, a seventh up-sampling network, an eighth up-sampling network, and a ninth-network. An input of the regression model may be used as an input of the first down-sampling network, an output of the first down-sampling network may be used as an input of the second down-sampling network, an output of the second down-sampling network may be used as an input of the third down-sampling network, . . . , and so on, with the output of the eighth up-sampling network as the input of the ninth network, and the output of the ninth network as the final output of the regression model.

In some embodiments, the processor may splice the sample scan image, the sample target region contour image, and the sample weighted image according to a direction of a channel dimension to obtain the sample initial image.

The first down-sampling network may be configured to extract features of the initial image of the sample, and perform a down-sampling on the extracted features to obtain a first feature image.

In some embodiments, the first down-sampling network may include two convolutional blocks, a down-sampling layer, and two convolutional blocks sequentially connected. An input of the first down-sampling network may serve as an input of a first convolutional block, an output of the first convolutional block may serve as an input of a second convolutional block, an output of the second convolutional block may serve as an input of the down-sampling layer, an output of the down-sampling layer may serve as an input of the third convolutional block, an output of the third convolutional block may serve as an input of the fourth convolutional block, and an output of the fourth convolutional block may serve as the final output of the first down-sampling network.

In some embodiments, the convolutional block in the first down-sampling network may include at least one or any combination of a convolutional kernel, a normalization function, and an activation function, etc. A size of the convolution kernel may be 3×3 with the filling of 1, the step size of 1 by default, the normalization function may be a batch normalization (BN) function, and the activation function may be an ReLU function.

In some embodiments, the first convolutional block and the second convolutional block in the first down-sampling network may be configured to increase a count of input channels. In some embodiments, the processor may obtain a first sub-feature image based on the first convolutional block, the second convolutional block in the first down-sampling network.

In some embodiments, the down-sampling layer in the first down-sampling network may reduce a size of the first sub-feature image based on the maximum pooling. For example, the down-sampling layer may cause a size of the output image to be reduced to half the size of the first sub-feature image.

The count of the convolution blocks and the down-sampling layers, as well as the count of convolution kernels, normalization functions, and activation functions in the convolution blocks in the above-described first down-sampling network are provided only as examples and are not limiting.

In some embodiments, the second down-sampling network, the third down-sampling network, and the fourth down-sampling network may be a structure similar to the first down-sampling network.

In some embodiments, the second down-sampling network may be configured to extract features of the first feature image and perform down-sampling on the extracted features to obtain a second feature image. The third down-sampling network may be configured to extract the features of the second feature image and perform down-sampling on the extracted features to obtain a third feature image. The fourth down-sampling network may be configured to extract the features of the third feature image and perform down-sampling on the extracted features to obtain the fourth feature image.

In some embodiments, the processor may obtain a second sub-feature image based on the first convolutional block and the second convolutional block in the second down-sampling network. In some embodiments, the processor may obtain a third sub-feature image based on the first convolutional block and the second convolutional block in the third down-sampling network. In some embodiments, the processor may obtain a fourth sub-feature image based on the first convolutional block and the second convolutional block in the fourth down-sampling network.

In some embodiments, the fifth up-sampling network may include an up-sampling layer and two convolutional blocks connected in sequence. An input of the fifth up-sampling network may serve as an input of the up-sampling layer, an output of the up-sampling layer may serve as an input of the first convolution block, an output of the first convolution block may serve as an input of the second convolution block, and an output of the second convolution block may serve as the output of the final output of the fifth up-sampling network.

In some embodiments, the up-sampling layer in the fifth up-sampling network may enlarge a size of the fourth feature image to obtain a fifth sub-feature image through a bilinear interpolation method. For example, the down-sampling layer may cause the output fifth sub-feature image to be enlarged to double the size of the fourth feature image.

In some embodiments, the fifth up-sampling network may splice a fifth sub-feature image output from the up-sampling layer with a fourth sub-feature image in the direction of the channel dimension to obtain a fifth spliced image, and then input the fifth spliced image into the first convolutional block after the up-sampling layer.

In some embodiments, the convolutional block in the fifth up-sampling network may include any one or combination of the convolutional kernel, the normalization function, and the activation function. The size of the convolution kernel may be 3×3, the normalization function may be a bn function, and the activation function may be an ReLU function.

In some embodiments, the first convolutional block and the second convolutional block in the fifth up-sampling network may be respectively configured to reduce a count of input channels. In some embodiments, the processor may obtain a fifth feature image based on the fifth spliced image by the first convolutional block and the second convolutional block in the fifth up-sampling network.

The count of the convolutional blocks and the down-sampling layers, as well as the count of convolutional kernels, normalization functions, and activation functions of the convolutional blocks in the above-described fifth up-sampling network, are intended to be exemplary only and not limiting.

In some embodiments, the sixth up-sampling network, the seventh up-sampling network, and the eighth up-sampling network may have structures similar to the fifth up-sampling network.

In some embodiments, the sixth up-sampling network may be configured to up-sample the fifth feature image and perform a feature extraction on the results of the up-sampling to obtain a sixth feature image. The seventh up-sampling network may be configured to up-sample the sixth feature image and perform the feature extraction on the results of the up-sampling to obtain a seventh feature image. The eighth up-sampling network may be configured to up-sample the seventh feature image and perform the feature extraction on the result of the up-sampling to obtain an eighth feature image.

In some embodiments, the sixth up-sampling network may process the fifth feature image through an up-sampling layer to output a sixth sub-feature image; splice the sixth sub-feature image output from the up-sampling layer with the third sub-feature image in the direction of the channel dimension to obtain a sixth spliced image, and input the sixth spliced image into the convolution block after the up-sampling layer to obtain the sixth feature image. The convolution block may be a plurality of convolution blocks connected sequentially, such as 2 convolution blocks connected sequentially.

In some embodiments, the seventh up-sampling network may process the sixth feature image through the up-sampling layer to output a seventh sub-feature image; splice the seventh sub-feature image output by the up-sampling layer with the second sub-feature image in the direction of the channel dimension to obtain a seventh spliced image, and input the seventh spliced image into the convolution block after the up-sampling layer to obtain the seventh feature image. The convolution block may be a plurality of convolution blocks connected sequentially, such as 2 convolution blocks connected sequentially.

In some embodiments, the eighth up-sampling network may process the seventh feature image through the up-sampling layer to output an eight sub-feature image; splice the eighth sub-feature image output from the up-sampling layer with the first sub-feature image in the direction of the channel dimension to obtain an eighth spliced image, and input the eighth spliced image into the convolution block after the up-sampling layer to obtain the eighth feature image. The convolution block may be a plurality of convolution blocks connected sequentially, such as 2 convolution blocks connected sequentially.

In some embodiments, the fifth sub-feature image may have the same dimension as the fourth sub-feature image, the sixth sub-feature image may have the same dimension as the third sub-feature image, the seventh sub-feature image may have the same dimension as the second sub-feature image, and the eighth sub-feature image may have the same dimension as the first sub-feature image.

The ninth network may be configured to process the eighth feature image and output the dose prediction result.

In some embodiments, the ninth network may include the convolutional block.

In some embodiments, the convolutional block of the ninth network may include a 1×1 convolutional kernel. The convolutional block of the ninth network may be configured to reduce the count of input channels.

The regression training refers to a process of training a model using the features of the existing input data and the corresponding output data, so that the model learns a specific association between the inputs and the corresponding outputs.

In some embodiments, the training process may include: inputting the plurality of first training samples with the first labels into the initial regression model, constructing the loss function through the first label and an output of the initial regression model, iteratively updating, based on the loss function, parameters of the initial regression model by gradient descent or other method. The model training may be completed when a termination condition is satisfied, and the trained regression model may be obtained. The termination condition may be that the loss function converges, a count of iterations reaches a threshold, etc.

The loss function may be configured to assess a difference between a predicted output of the regression model (e.g., the dose prediction result) and a desired output (e.g., the sample dose data). In some embodiments, the loss function may be a mean square error (MSE) loss function, a cross-entropy loss function, etc., or any combination thereof.

In some embodiments of the present disclosure, by setting up the convolution operation, the down-sampling operation, the up-sampling operation, etc. in the regression model, the feature extraction may be carried out for the to-be-tested scan image, the to-be-tested target region contour image, and the to-be-tested weighted image after the dimensionality reduction, so as to reduce the dimensionality of the features while retaining the effective information.

In some embodiments, the processor may determine, based on the sample dose data, a classification result of each voxel through a binary classification model, and screen a dose region as input data for the regression training.

The binary classification model refers to a model configured to discriminatively classify data.

In some embodiments, the binary classification model may be a machine learning model, e.g., the binary classification model may include one of a logistic regression model, a support vector machine, or other classification model. In some embodiments, the binary classification model may also be a neural network model.

In some embodiments, an input to the binary classification model may include the sample dose data and an output may include the classification result. The classification result refers to the result of determining each dose value in the sample dose data. In some embodiments, the classification result may be a binary image that is consistent in size with the sample dose data. In some embodiments, the classification result may include at least one of a no dose region and a dose region. The no dose region may indicate a region including voxels or pixels in the sample dose data whose dose values are less than a preset threshold, and the dose region may indicate a region including voxels or pixels in the sample dose data whose dose values are greater than or equal to the preset threshold. In some embodiments, the no dose region or the dose region may be indicated by a 0 or 1. For example, 0 may indicate the no dose region and 1 may indicate the dose region. The preset threshold may be determined based on experimentation or experience, e.g., the preset threshold may be 0.

In some embodiments, the binary classification model may be obtained by training in various feasible ways based on a great count of second training samples with second labels. For example, the parameter updating may be performed based on the gradient descent. The training of the binary classification model may be similar to the training process of the regression model. For more contents, please refer to the related descriptions above.

In some embodiments, the second training sample may include the sample dose data. The second training sample may be obtained based on historical data.

In some embodiments, the second label may include the classification result for each voxel in the sample dose data. The second label may be obtained based on manual labeling.

In some embodiments, the processor may perform an operation on the dose region and the dose prediction results output from the initial regression model based on an inter-element multiplication, establish the loss function based on the results of the operation and the sample dose data, and, iteratively update, based on the loss function, parameters of the initial regression model.

In some embodiments of the present disclosure, the input data for the binary classification model and the regression model may be at least partially the same, and the sample dose data may serve as the training data in the binary classification model, and as the labels in the regression model. The loss function of the regression model may be constructed based on a difference between the result after the operation and the sample dose data, which is conducive to improving the prediction accuracy of the regression model in a specific dose region. The loss function may guide a direction of updating the model parameters, which enables the model to converge to the optimal solution faster during the training process, reduces a count of ineffective iterations and the amount of calculation, and thus further reduces the amount of training of the model and improves the training efficiency.

Step 270, obtaining a dose prediction result by inputting a to-be-tested scan image, a to-be-tested target region contour image, and a to-be-tested weighted image after the dimensionality reduction into the trained regression model.

The dose prediction result refers to a predicted distribution of a magnitude of radiation dose received at different positions within the object. In some embodiments, the dose prediction result may be 2D or 3D data configured to visualize the spatial distribution of the dose within the object.

In some embodiments, the processor may input the to-be-tested scan image, the to-be-tested target region contour image, and the to-be-tested weighted image after dimensionality reduction into the trained regression model to obtain the dose prediction result.

In some embodiments, the processor may calculate a target function for the target region and the OAR based on the dose prediction result to accomplish an automatic plan optimization, the target function may include Equation (5):

$$F_{obj} = \sum_j \alpha_j * (d_j - p_j)^2; \tag{5}$$

where, $d_j$ denotes a calculated dose at the jth point, $p_j$ denotes a dose value at the jth point in the dose prediction result, and $\alpha_j$ denotes a constraint penalty factor at the jth point. By calculating the minimal value of the target function $F_{obj}$, the calculated dose $d_j$ corresponding to each point in the dose prediction result may be obtained; and a target radiotherapy plan may be obtained by optimizing an original radiotherapy plan based on the calculated dose $d_j$.

The calculated dose refers to a value of the dose at each position associated with an intensity of radiation when the radiation therapy is performed.

In some embodiments, a radiation field intensity image may be determined based on the calculated dose. The radiation field intensity image may be configured to indicate the distribution of radiation intensity at different positions within a radiation field.

In some embodiments, the calculated dose corresponding to different positions may cause different values of the constraint penalty factor. The processor may obtain the value of the constraint penalty factor based on a determination rule. Exemplarily, the determination rule may be as follows: the calculated dose corresponds to a position in the OAR, where $\alpha_j$ may be a non-zero value when $d_j > p_j$, and $\alpha_j$ may be zero when $d_j < p_j$; the calculated dose corresponds to a position in the target region planned target volume (PTV), where $\alpha_j$ may be a non-zero value when $d_j < p_j$, and $\alpha_j$ may be zero when $d_j > p_j$.

The original radiotherapy plan refers to a radiotherapy plan that is originally developed for the object, which is based on the diagnosis, the position, size, and shape of the lesion of the patient, and other related medical images. For example, the original radiotherapy plan may include a direction of the radiation field and an intensity distribution of the radiation field, etc.

The dose data refers to a total energy of the radiation received at different positions, while the radiation field intensity refers to the intensity of the radiation received at each position in different directions.

In some embodiments, the processor may obtain, from the terminal device, a radiotherapy plan made for the object by a user (e.g., a radiation oncologist, a radiographer, a physicist, etc.).

The target radiotherapy plan refers to a result of further optimization and improvement based on the original radiotherapy plan.

In some embodiments, the processor may determine the radiation field intensity image based on the calculated dose $d_j$ at each point in the to-be-tested scan image; perform an evaluation based on the radiation field intensity image to check whether the radiation intensity at each position satisfies the intensity distribution of the radiation field. In response to the radiation intensity does not satisfy the intensity distribution of the radiation field, the original radiotherapy plan may be optimized accordingly to obtain the target radiotherapy plan. The optimization process may include adjusting an angle, a size, a shape, and a dose distribution of the radiation field of the original radiotherapy plan. The radiation field intensity image may be configured to reflect the intensity distribution of different rays within the radiation field.

In some embodiments, the processor may determine the radiation field intensity image in various manners. For example, the processor may generate the radiation field intensity image based on a third-party system, for example, a radiation treatment planning system (TPS) may be used to generate, based on the calculated dose $d_j$ at each point in the to-be-tested scan image, the radiation field intensity image.

In some embodiments of the present disclosure, by constructing the target function, the target function may be minimized, thereby obtaining the radiation field intensity image of the dose prediction result, which is conducive to optimizing and improving the radiation field direction and the intensity distribution of the radiation field in an intensity-modulated conformal radiotherapy, so as to improve the quality and efficiency of treatment.

In some embodiments of the present disclosure, by analyzing the to-be-tested scan image, the to-be-tested target region contour image, and the to-be-tested weighted image after dimensionality reduction by regression model, the dose prediction result may be efficiently and accurately obtained, which is conducive to automatically optimizing the original radiotherapy plan step by step, improving the efficiency of optimizing radiotherapy plan, and saving a lot of time and energy for the user, so as to make the generated treatment plan more in line with clinical needs and user requirements.

It may be noted that the foregoing description of the process 200 is intended to be merely exemplary and illustrative, and does not limit the scope of application of the present disclosure. For those skilled in the art, various corrections and changes may be made to the process 200 under the guidance of the present disclosure. However, these corrections and changes remain within the scope of the present disclosure.

Figure 3:
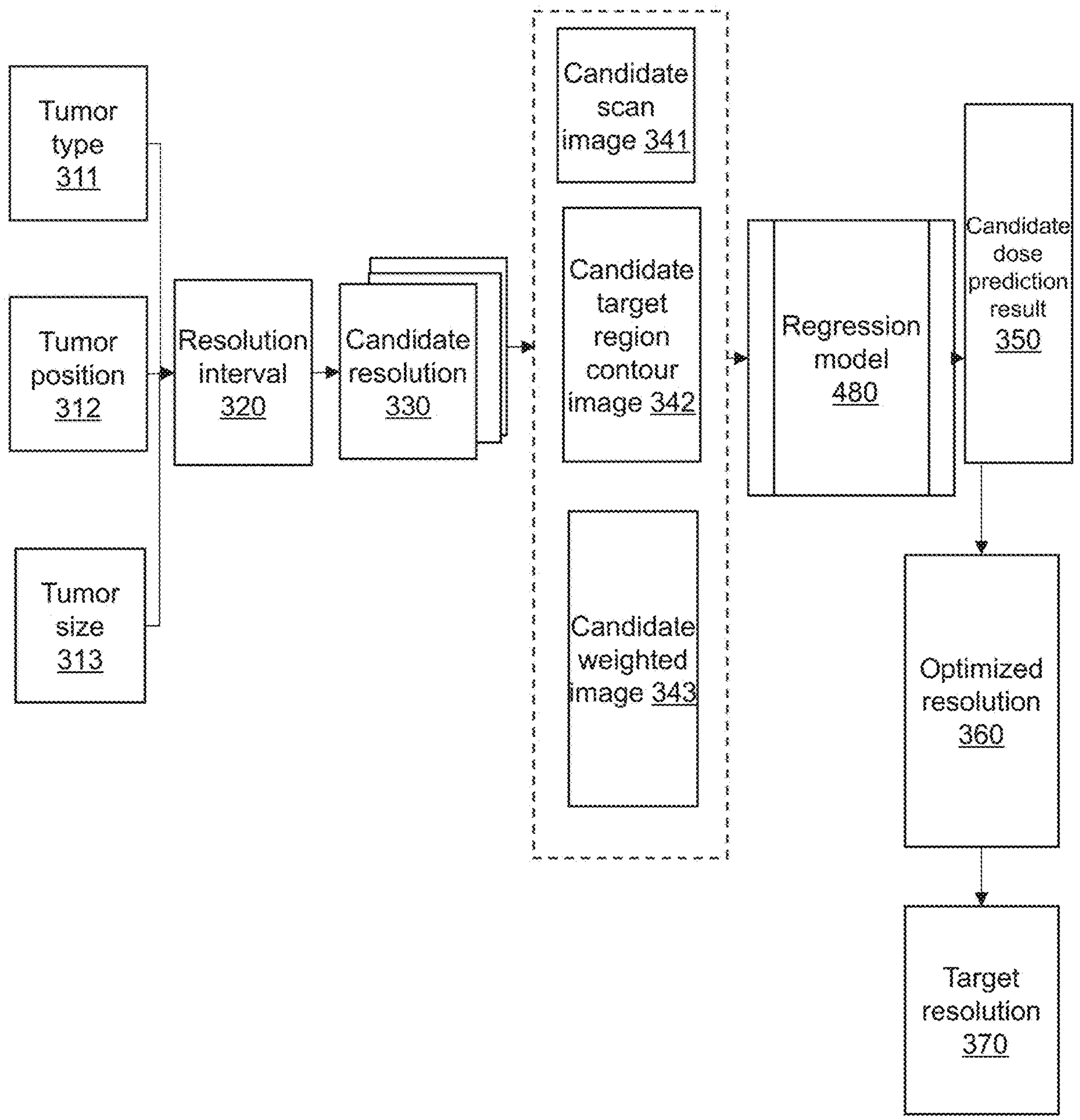
FIG. 3 is a schematic diagram illustrating an exemplary process for determining a target resolution according to some embodiments of the present disclosure.

FIG. 3 is a schematic diagram illustrating an exemplary process for determining a target resolution according to some embodiments of the present disclosure.

In some embodiments, a resolution of a to-be-tested scan image may be determined based on a tumor type 311, a tumor position 312, and a tumor size 313 corresponding to the to-be-tested scan image, as shown in FIG. 3.

For more contents on the to-be-tested scan image and the resolution, please refer to the related descriptions in FIG. 2.

The tumor type, the tumor position, and the tumor size may be important parameters configured to describe and analyze tumors. The tumor type refers to a histological classification of the tumor. For example, the tumor type may include a benign tumor (e.g., a lipoma, an adenoma), a malignant tumor (e.g., an adenocarcinomas, a sarcoma), and a junctional tumor (e.g., a certain neuroendocrine tumor), etc.

The tumor position refers to a specific portion of the tumor within the object. For example, the tumor position may include coordinate data of the tumor within the body.

It may be noted that due to a presence of some tumors (e.g., malignant epithelial tumors) distributed throughout the body, and a quality of the to-be-tested scan image obtained may vary with different configurations throughout the body, a difference in the tumor position may have an impact on the resolution of resampling.

The tumor size refers to a volume or dimension of the tumor in the body.

In some embodiments, the processor may obtain the tumor type, the tumor position, and the tumor size corresponding to the to-be-tested scan image by reading from a storage device, a database, calling a data interface, etc.

In some embodiments, the processor may determine the resolution based on the tumor type, the tumor position, and the tumor size corresponding to the to-be-tested scan image in various manners. For example, the processor may determine the resolution through a preset table or vector database constructed based on historical data. The preset table/vector database may be a table or database indicating a correspondence of the tumor type, the tumor position, and the tumor size corresponding to different to-be-tested scan images and different resolutions.

It may be noted that an amount of information required by different types of tumors to be used for data analysis is different, and different resolutions result in different detailed information and different contextual information in the to-be-tested scan image after resampling, so it may be necessary to choose an appropriate resolution to take into account a problem of balancing the detailed information and the contextual information.

In some embodiments, as shown in FIG. 3, the processor may determine a resolution interval 320 based on the tumor type 311, the tumor position 312, and the tumor size 313; generate a plurality of candidate resolutions 330 based on the resolution interval 320; and determine a target resolution 370 based on the plurality of candidate resolutions 330.

The resolution interval refers to a series of resolution values or ranges.

In some embodiments, the processor may determine the resolution interval based on a priori knowledge or historical data.

In some embodiments, the processor may determine the resolution interval based on the tumor type, the tumor position, and the tumor size corresponding to the to-be-tested scan image. For example, the processor may determine the resolution interval by checking up a table constructed based on a correspondence between the tumor type, the tumor position, the tumor size of the different to-be-tested scan image and the different medium-resolution curvilinear edges in the historical data.

The candidate resolution refers to the resolution to be determined as the target resolution.

In some embodiments, the processor may determine the candidate resolution in various manners. For example, the processor may obtain the candidate resolution by randomly selecting from the resolution interval.

In some embodiments, the processor may determine the target resolution based on the plurality of the candidate resolutions in various manners. For example, the processor may count a count of historical uses of the plurality of the candidate resolutions, and determine the candidate resolution with the highest count of historical uses as the target resolution.

In some embodiments of the present disclosure, generating the plurality of the candidate resolutions instead of directly selecting a fixed resolution may provide more options for subsequent decision-making and increase a flexibility of processing. By determining the target resolution from the candidate resolutions, the most suitable resolution may be selected under a premise of ensuring quality, thereby avoiding a waste of resources caused by too high or too low resolution, so as to improve the efficiency of the entire processing.

In some embodiments, as shown in FIG. 3, for each of the candidate resolutions 330, the processor may perform resampling based on the candidate resolution 330 to obtain a corresponding candidate scan image 341, a candidate target region contour image 342, and a candidate weighted image 343. The processor may determine, based on the candidate scan image 341, the candidate target region contour image 342, and the downscaled candidate weighted image 343, a candidate dose prediction result 350 corresponding to the candidate resolution by a regression model 480. The processor may further determine, based on the candidate resolution 330 and the candidate dose prediction result 350 corresponding to the candidate resolution, an optimized resolution 360; and determine, based on the optimized resolution 360, the target resolution 370.

The candidate scan image and a candidate contour image respectively refer to the results of resampling the to-be-tested scan image, and a to-be-tested contour image, based on the candidate resolution. The candidate contour image may include a candidate target region contour image, and a candidate OAR contour image. To-be-tested dose data refers to the dose data corresponding to the to-be-tested scan image.

For more contents on the to-be-tested contour image, the to-be-tested dose data, and the resampling, please refer to the related descriptions in FIG. 2.

In some embodiments, for each of the candidate resolutions, the processor may resample, based on the candidate resolution, the candidate scan image and the candidate contour image by a manner similar to the manner of obtaining the sample scan image in FIG. 2 to obtain the corresponding candidate scan image and the candidate contour image. The processor may further determine, based on the weighted image corresponding to the candidate contour image, the candidate weighted image by the dimensionality reduction similar to the manner in FIG. 2.

In some embodiments, for each of the candidate resolutions, the processor may input the candidate scan image, the candidate target region contour image, and the downscaled candidate weighted image into the trained regression model, to obtain a dose prediction result corresponding to the candidate resolution.

For more contents on the regression model, please refer to the related description in FIG. 2.

The optimized resolution refers to the resolution selected from the candidate resolutions to determine the target resolution.

It may be noted that similar candidate resolutions have similar resampling results, and thus the corresponding dose prediction results may also be similar. The processor may traverse each of the candidate resolutions in turn, and if a difference between the dose prediction results of the candidate resolutions and the dose prediction results of adjacent candidate resolutions is great, the candidate resolution may be rejected. The neighboring may be the candidate resolution that is numerically adjacent.

In some embodiments, the processor may arrange the plurality of the candidate resolutions from smallest to greatest, and for each of the candidate resolutions, a difference between the dose prediction result corresponding to the selected candidate resolution and the dose prediction result of the previous candidate resolution, and a difference between the dose prediction result and the next candidate resolution may be calculated respectively, and if the difference is greater than the difference threshold, the candidate resolution may be rejected. The processor may perform the above operation for each of the candidate resolutions, reject the candidate resolution with the difference greater than the difference threshold, and use the remaining candidate resolutions as the optimized resolutions. The previous candidate resolution refers to the candidate resolution that is smaller than and adjacent to the selected candidate resolution. The next candidate resolution refers to the candidate resolution that is greater than the selected candidate resolution and is adjacent to the selected candidate resolution. The difference threshold may be manually preset.

The target resolution refers to the resolution configured to resample the to-be-tested scan image.

In some embodiments, the processor may select the target resolution from the optimized resolutions by random selection. In some embodiments, the processor may score the dose prediction results corresponding to the plurality of the candidate resolutions via a scoring layer, and take the one with the greatest score as the target resolution. For more contents on the scoring layer, please refer to the related descriptions of FIG. 4.

In some embodiments of the present disclosure, by generating the corresponding dose prediction result for each of the candidate resolutions, the dose distribution at different resolutions may be more accurately predicted, and more valuable reference information may be provided to physicians and therapists. By determining the optimized resolution based on the dose prediction results, time and cost of trying different resolutions may be greatly reduced, and the decision-making efficiency and the efficiency of the whole treatment process may be improved. By introducing the dose prediction and the decision-making mechanism based on the prediction results, the accuracy, efficiency, and interpretability of the medical image processing may be further improved.

In some embodiments of the present disclosure, determining the resolution interval by considering the tumor type, the tumor position, and the tumor size may ensure that the selected resolution is more adapted to the specific medical scenarios and needs, and the accuracy of the diagnosis and treatment may be improved. Determining the resolution through the multi-factor manner helps to easily perform the adjustment and optimization to adapt to new needs and technological developments.

Figure 4:
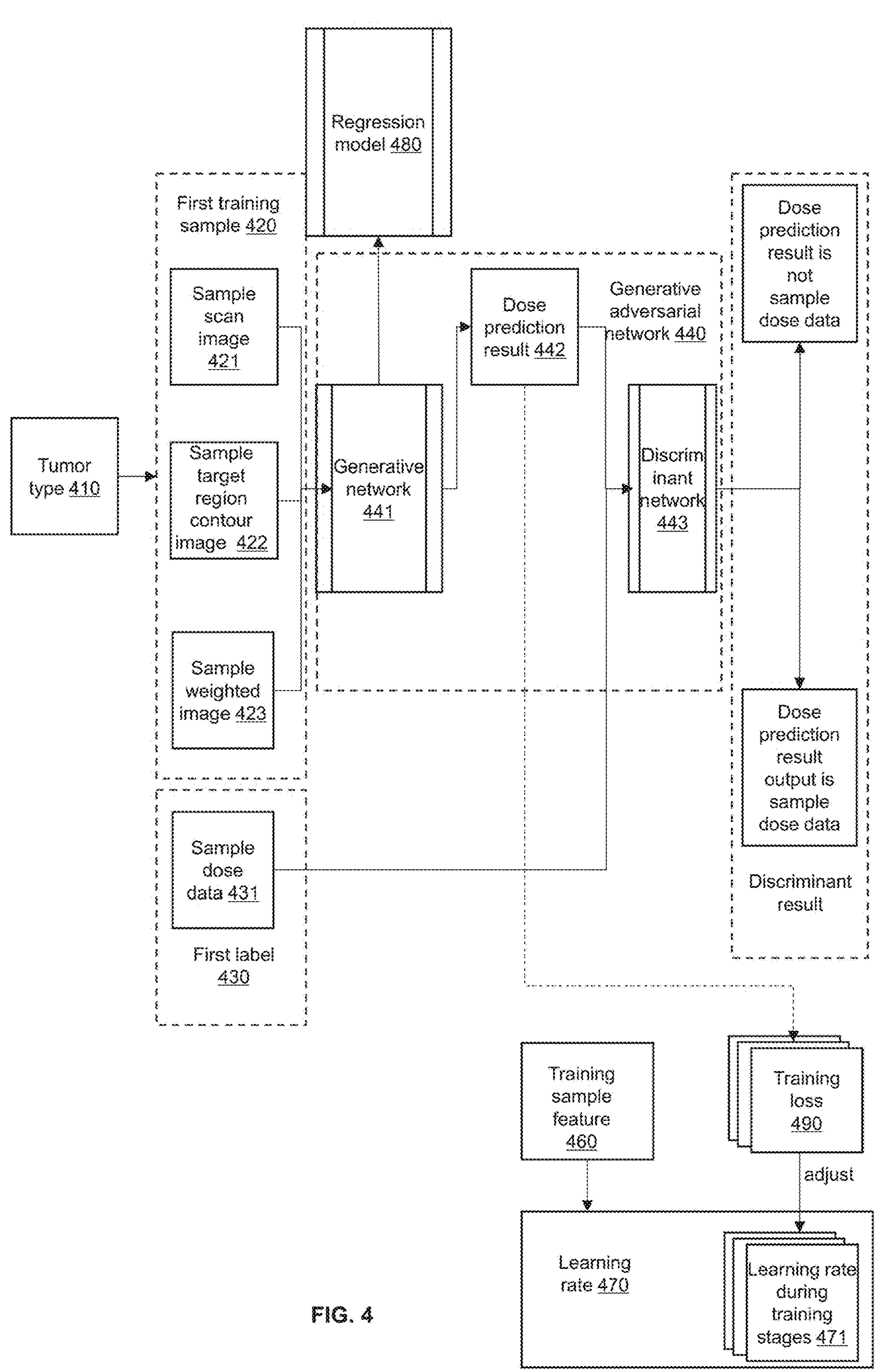
FIG. 4 is a schematic diagram illustrating an exemplary adversarial training according to some embodiments of the present disclosure.

FIG. 4 is a schematic diagram illustrating an exemplary adversarial training according to some embodiments of the present disclosure.

In some embodiments, as shown in FIG. 4, the regression model 480 may be implemented based on a generative network 441, and a processor may train, based on a first training sample 420, a discriminant network 443 and the regression model 480 by means of a generative adversarial network 440.

For more contents on the regression model and the first training sample, please refer to the descriptions of FIG. 2.

The adversarial training may be performed using a generative adversarial network (GAN). The GAN may include the generative network and the discriminant network.

The generative network may be configured to generate a dose prediction result. In some embodiments, the generative network may be a convolutional and transformer-based generative network, a convolutional neural network model, or a recurrent neural network model, etc.

The discriminant network may be configured to discriminate whether the dose prediction result input is dose data. In some embodiments, the discriminant network may be the discriminant network in a network such as PatchGan.

In some embodiments, the generative adversarial network may be trained based on a great count of the first training samples. The training samples may include a sample scan image, a sample target region contour image, a sample weighted image, and sample dose data corresponding to the sample scan image.

The training of the generative adversarial network may include a plurality of stages.

In some embodiments, the parameters of an initial generative adversarial network may be obtained in various manners. For example, the parameters of the initial generative adversarial network may be obtained by random initialization.

First stage: fixing parameters of the generative network and training the discriminant network.

The sample scan image, the sample target region contour image, and the sample weighted image may be input into the generative network to generate the dose prediction result. The generated dose prediction result may form a set of data pair with the sample scan image, the sample target region contour image, and the sample weighted image (with a label 0), and then the sample scan image, the sample target region contour image, the sample weighted image, and the corresponding sample dose data may form another set of data pair (with a label 1). The two aforementioned data pairs may be used as the training data for training the discriminant network, so that the discriminant network may discriminate between the sample dose data and the generated dose prediction result as much as possible.

Second stage: fixing the parameters obtained in the first stage by the discriminant network and training the generative network.

The generative network and the discriminant network obtained in the first stage may be spliced into a composite model, and the sample scan image, the sample target region contour image, and the sample weighted image may be input to the composite model. The composite model may output the discriminative result (including 0 or 1, with 0 indicating that the dose prediction result output by the generative network is not the sample dose data, and 1 indicating that the dose prediction result output by the generative network is the sample dose data). The (1-discriminative result) may be used as a loss function of the composite model. The loss function may be used to update the parameters of the generative network based on a gradient descent method.

With the continuous training in the second stage, the more times the composite model outputs a result of 1 or the more times the composite model outputs a result of 1 consecutively, the stronger an ability for the generative network to output the dose prediction results that are similar to the real sample dose data, and the similarity between the output of the dose prediction results of the generative network and the sample dose data may increase.

Then loop the first stage and the second stage, and eventually, through continuous loops, the generative network and the discriminant network may become more and more powerful, and eventually the model may converge, i.e., a value of the loss function corresponding to the various stages may be minimized or gradually tends to zero, the trained generative adversarial network may be obtained, and the trained generative network may be used as the regression model. For example, the processor may train the generative network as well as the discriminant network alternately according to the loss functions corresponding to the various stages. Specifically, when training the discriminant network, the parameters of the discriminant network may be adjusted to minimize a second loss function while the parameters of the generative network are fixed. When training the generative network, with the parameters of the discriminant network fixed, the parameters of the generative network may be adjusted to minimize a first loss function. The first loss function may be configured to reflect the difference between the output of the generative network and the sample dose data. The second loss function may be configured to measure an ability for the discriminant network to discriminate between the sample dose data and the dose prediction results.

In some embodiments, as shown in FIG. 4, the processor may determine different first training samples 420 and corresponding first labels 430 based on a tumor type 410; alternately train the regression model based on the first training samples with different scale sizes. The different first training samples may have different learning rates 470 during the training process, and the learning rates 470 may be adjusted based on a training sample feature 460.

For more contents on the first training sample and the first label, please refer to the descriptions in FIG. 2.

For more contents about the tumor type, please refer to the descriptions in FIG. 3.

The first training sample refers to a set of at least a portion of the samples used to train an initial regression model.

It may be noted that there are differences in radiotherapy plans for different types of tumors, so different tumor types need to correspond to their respective training sample sets.

In some embodiments, as shown in FIG. 4, the processor may obtain, based on historical data, the first training samples 420 corresponding to the different tumor types as well as the corresponding first labels 430. For example, the processor may perform, based on the historical data, a statistical analysis to take the sample scan image 421, the sample target region contour image 422, and the sample weighted image 423 of the same tumor type as the first training sample 420 of the tumor type, and take the sample dose data 431 according to the sample scan image as the first label 430.

The scale size refers to a count of the training samples in the training sample set.

In some embodiments, the processor may count the count of the training samples within each first training sample to determine the scale size of each first training sample.

The learning rate refers to a parameter configured to control a magnitude of weight updates in a machine learning algorithm. In some embodiments, the learning rate may be a configurable parameter used in the training of a neural network. The learning rate may usually have a small positive value. For example, the learning rate may be in a range of between 0.0 and 1.0. The weight may be a parameter used in the neural network model to calculate and estimate a relationship between input and output samples.

In some embodiments, the processor may take an initial value of an adjustment parameter set for the initial regression model as the learning rate, which is dynamically adjusted as the training proceeds, e.g., using a method such as learning rate decay or a self-adaptive learning rate, etc., to adapt to learning needs of the model at different stages.

The training sample feature refers to data reflects features of the first training sample itself. For example, the training sample feature may include the tumor type corresponding to the first training sample, a numerical percentage and a reliability for all of the first training samples, etc.

The numerical percentage for all of the first training samples refers to a percentage of a count of the training samples in the first training samples corresponding to a particular tumor type.

The reliability refers to the reliability corresponding to each of the different first training samples. In some embodiments, the processor may determine the reliability of the different first training samples based on manual input. In some embodiments, the processor may also assess the reliability of the first training samples by identifying outliers in the first training samples, e.g., the greater the percentage of outliers in the first training samples, the lower the reliability of the first training sample.

In some embodiments, there may be a consistency in a presence of labels corresponding to the same or similar first training samples. The processor may obtain the labels of the first training samples corresponding to a certain tumor type, and determine whether the count of consistent labels is greater than a quantity threshold. In response to that the count of consistent labels is greater than a quantity threshold, the processor may determine that the reliability is high, and the training effect is better; in response to that the count of consistent labels is smaller than the quantity threshold, the processor may determine that the same or similar first training samples correspond to the sample dose data with great differences, and that the reliability is low, the training effect is poor.

In some embodiments, the processor may determine the training sample feature in various manners.

In some embodiments, the processor may adjust the learning rate based on the training sample feature in various manners. For example, the processor may generate a retrieval vector based on the training sample feature, perform a search in a database based on the retrieval vector, determine a reference vector that meets a match criteria, determine the reference vector that meets the match criteria as a target vector, and determine the reference learning rate corresponding to the target vector as an actual learning rate.

The match criteria refers to a determination condition for determining the target vector. The match criteria may include a similarity with the retrieved vector being greater than a similarity threshold or being a maximum similarity, etc. There may be various manners to calculate the similarity, such as a Euclidean distance, a cosine distance, etc.

The database refers to a database for storing, indexing, and querying vectors. The database may store a plurality of reference vectors and the reference learning rate corresponding to each of the reference vectors.

In some embodiments, the database may be obtained based on the historical data. For example, the processor may determine historical training sample features for different types of the first training samples as reference vectors based on the historical data. The reference learning rate may be a historical learning rate corresponding to the historical training sample feature that make the loss function to converge toward a minimal value in a fastest way.

In some embodiments, the learning rate may change dynamically as the training proceeds, and the learning rate 470 may be a sequence of data including the learning rates during a plurality of training stages 471. For more contents on the different learning rates during the training stages, please refer to the related descriptions below.

The alternately training refers to training the regression model with the different first training samples alternately during the training process of the regression model to improve a generalization ability and a performance of the regression model.

In some embodiments, taking the training of the regression model as an example, the alternately training may include: sorting all of the first training samples in a preset order (e.g., from large to small, from small to large) based on the scale size, performing a plurality of rounds of iterations, and obtaining a trained regression model based on the iteration results.

The at least one round of iteration may include: training the regression model of the current round of iteration based on the first training sample of the current round of iteration, constructing a loss function based on the corresponding labels and the output result of the regression model of the current round of iteration, iteratively updating the parameters of the initial regression model based on the loss function by the gradient descent or other methods; when the termination conditions are met, the model training may be completed, and the trained regression model of the current round of iteration may be obtained; in response to that the iteration conditions are met, the iteration may end, and the regression model of the current round of iteration may be taken as the trained regression model; in response to that the iteration conditions are not met, the regression model of the current round of iteration may be taken as the regression model of the next round of iteration, and a first training sample ranked next to the first training sample of the current round of iteration may be selected as the first training sample of the next round of iteration to continue for the next round of iteration.

The iteration condition refers to a determination condition that evaluates whether an iteration of the alternately training stops. In some embodiments, the iteration condition may include that a count of iterative updates reaches a times threshold, all of the first training samples are selected, etc. The times threshold may be a system default, a system preset, etc.

In some embodiments of the present disclosure, for the different tumor types, the processor may select the first training samples associated with them to ensure that the regression model is able to learn the feature and pattern of the type of tumor, and to improve the accuracy and effectiveness of the model. Samples of different scales may bring different amounts of information and complexities, which help the model to generalize better. The processor may adjust the learning rate according to the features of the first training samples to make the regression model more flexible and efficient during the training process. For example, for the samples with obvious features, the learning rate may be appropriately increased to speed up the training, and for the samples with obscure features, the learning rate may be appropriately lowered to ensure that the regression model is able to fully learn.

In some embodiments, the learning rate 470 may include learning rates 471 during a plurality of training stages, as illustrated in FIG. 4. Each of the learning rates 471 during training stages for the plurality of training stages may be updated based on a training loss 490 for the training stages.

In some embodiments, the trained regression model may be obtained by training through the plurality of training stages. In some embodiments, the processor may divide the entire training process of the regression model into a plurality of training stages based on preset rules. Exemplarily, the training process may include a plurality of iterations, with each iteration being each of the plurality of training stages.

It may be noted that each of the learning rates during the training stages may be preset by the database, and the learning rate may be dynamically adjusted as the training proceeds for better regression model adjustments and parameter updates.

The training loss may be configured to measure a difference between the dose prediction results of the regression model on the first training sample and the actual sample dose data. The different training stages may correspond to different values of the training loss.

In some embodiments, the processor may monitor the training loss for each training stage in real time, and when the training loss stops decreasing, the training stage may be determined as a target training stage, and the learning rate for the target training stage may be reduced.

In some embodiments, the processor may reduce the learning rate based on the target training stage with a preset proportion. For example, the learning rate may determine, based on a preset learning rate for the target training stage, a ratio value of the preset learning rate for the target training stage to the corresponding preset proportion, and the corresponding weights, a reduced learning rate by weighted summarization. The preset learning rate and the corresponding weights may be determined based on experimentation or experience.

The target training stage refers to the training stage when the training loss stops decreasing. Different target training stages may correspond to different preset ratios. As the training progresses, the preset proportion of the target training stages may be positively correlated with a count of consecutive occurrences of the target training stage.

For example, the preset ratio of the target training stage may be a product of the count of consecutive occurrences of the target training stage and a preset multiplier. Exemplarily, the preset multiplier may be 2, the preset ratio of a first target training stage may be 2, the preset ratio of a second target training stage may be 4, the preset ratio of a third target training stage may be 6, . . . , etc. The first target training stage, the second target training stage, the third target training stage, etc. may be the training stages in which the training loss stops decreasing in consecutive occurrences on a time axis, which corresponds to successive occurrences times of 1, 2, 3 . . . .

In some embodiments, when the training loss resumes decreasing after the training loss stops decreasing for the plurality of training stages, the processor may reduce the learning rate based on an exponential decay, a polynomial decay, etc.

In some embodiments, the processor may determine an initial sequence of the learning rates based on the training sample feature. The initial sequence of the learning rates may include initial learning rates for a plurality of stages. In the actual training process, the processor may monitor the training loss of each of the training stages, and when the training loss of a certain training stage (the target training stage) stops decreasing, the processor may adjust the initial learning rate based on the target training stage.

In some embodiments of the present disclosure, by assigning different weights to the ratio value of the learning rate of each of the target training stage to the corresponding preset proportion by a weighted average calculation, a relative importance of each value in an overall may be reflected, so as to ensure that the updated learning rate is between the greatest value and the smallest value in the weighting, thereby avoiding the learning rate from decreasing too fast.

In some embodiments of the present disclosure, for the different training samples, the different learning rates may be required, and through the learning rate adjustment, the regression model may self-adapt to the training samples to improve training efficiency and effectiveness.

Figure 5:
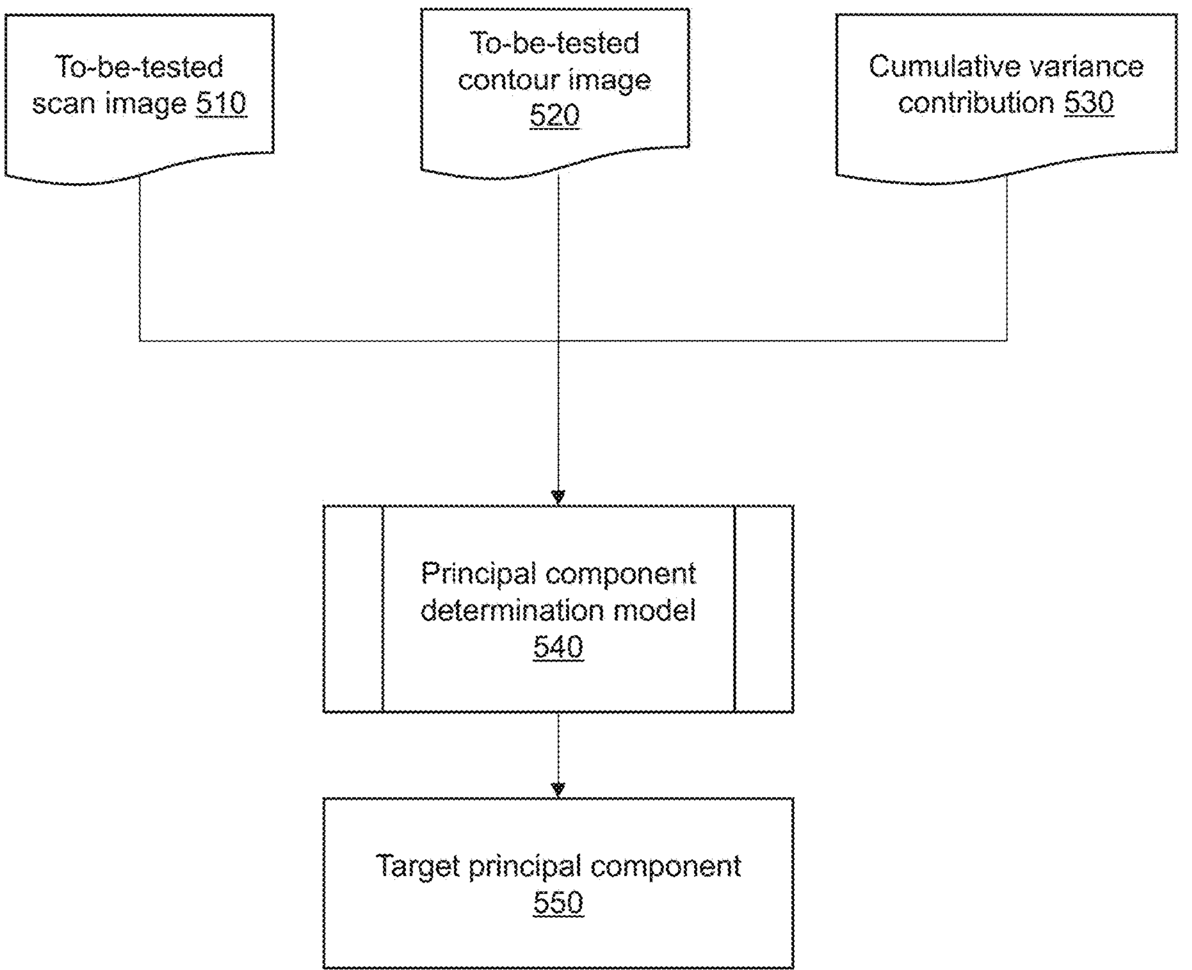
FIG. 5 is a schematic diagram illustrating an exemplary process for determining a target principal component according to some embodiments of the present disclosure.

FIG. 5 is a schematic diagram illustrating an exemplary process for determining a target principal component according to some embodiments of the present disclosure.

In some embodiments, the target principal component may be determined based on a contour image and a cumulative variance contribution.

For more contents on the contour image, please refer to the descriptions in FIG. 2.

In some embodiments, a preset condition may include the cumulative variance contribution satisfying a second proportion. For example, the processor may determine, based on the to-be-tested contour image, a corresponding distance image by calculating a shortest distance in a manner similar to FIG. 2; determine, based on the distance image, a corresponding weighted image by combining the corresponding to-be-tested organ image in the manner similar to FIG. 2. The processor may further sort, based on the weighted image, feature values from largest to smallest by determining the corresponding feature values and feature vectors in the manner similar to FIG. 2, calculate the proportion of each feature value among all feature values, and select the feature vector corresponding to feature values whose proportion is greater than the second proportion as the target principal component. The second proportion may be a system preset, a system default, etc.

In some embodiments, as shown in FIG. 5, the processor may determine a target principal component 550 of the to-be-tested contour image based on a contour image 520, and a cumulative variance contribution 530, by principal component determination model 540. The principal component determination model may be a machine learning model.

The principal component determination model refers to an algorithm or model configured to determine the target principal component.

In some embodiments, the principal component determination model may be trained in various feasible ways. For example, a parameter updating may be performed based on a singular value decomposition (SVD). Training the principal component determination model may be similar to training the regression model, as may be seen in the related descriptions in FIG. 2.

In some embodiments, the regression model may further include a scoring layer configured to score a dose prediction result. An inputs to the scoring layer may include the to-be-tested scan image, a to-be-tested target region contour image, a to-be-tested weighted image after a dimensionality reduction as well as the dose prediction result, and an output may include a score corresponding to the dose prediction result. In some embodiments, the scoring layer may be a machine learning model, such as the RNN, the DNN, etc.

In some embodiments, when the regression model includes the scoring layer, the first label may be a percentage of tumor regression after treatment based on the first training sample. The percentage of tumor regression may be determined based on a post-treatment target volume and a pre-treatment target volume. For example, the processor may calculate a difference between the post-treatment target volume and the pre-treatment target volume, and determine the percentage of tumor regression based on a ratio of the difference to the pre-treatment target volume.

In some embodiments, the score refers to a score that a user (e.g., a physician) or a model (e.g., the scoring layer) scores on the dose prediction results output by the current regression model. As a trained regression model is not yet available during the model training, the output of the training process may be unable to achieve the most accurate dose prediction for the sample scan images. In order to evaluate the performance of the regression model in the current training stage, the user may evaluate the dose prediction results of the current regression model, and use a level of the corresponding score to measure the current model performance.

In some embodiments, the score may be a numerical value. For example, the score may be from 1 to 5, and a higher score may represent better performance of the current regression model. In some embodiments, a basis for a high or low score may be determined based on, for example, the percentage of tumor regression after treatment based on the first training sample in different clinical scenarios. For example, the greater the percentage of regression of the tumor after treatment based on the first training sample, the higher the score of the corresponding dose prediction result.

In some embodiments of the present disclosure, the degree to which each principal component contributes to the variance of overall data may be shown by the cumulative variance contribution, which facilitates determining the target principal components that have a greater impact on the data, and improves the accuracy of the weighted image after the dimensionality reduction. The to-be-tested scan image may provide information about an internal structure of the object, while the to-be-tested contour image may describe a contour of the object or some specific regions. Combining these two types of images for the principal component analysis may provide a more comprehensive description of the internal organization and structural features of the object.

In some embodiments, a scan image may also be referred to as a CT image, and all of the foregoing are referred to as the scan image. A sample scan image may also be referred to as a resampled scan image, and all of the foregoing are referred to as the sample scan image. A sample contour image may also be referred to as a resampled contour image, and all of the foregoing are referred to as the sample contour image. Sample dose data may also be referred to as resampled dose data, and all of the foregoing are referred to as the sample dose data. A sample OAR image may also be referred to as a resampled OAR contour image, and all of the foregoing are referred to as the sample OAR image. The sample target region contour image may also be referred to as a resampled target region contour image, and all of the foregoing are referred to as the sample target region contour image. A weighted image may also be referred to as a weighted contour image based on distance weighting, or a weighted contour image, and all of the foregoing are referred to as the weighted image. A sample weighted image may also be referred to as a weighted contour image after the dimensionality reduction, and all of the foregoing are referred to as the sample weighted image. The to-be-tested scan image may also be referred to as a to-be-tested CT image, and all of the foregoing are referred to as the to-be-tested scan image. A to-be-tested target region contour image may also be referred to as a target region contour image to-be-tested, and all of the foregoing are referred to as the to-be-tested target region contour image. A to-be-tested weighted image may also be referred to as a weighted contour image to be tested, and all of the foregoing are referred to as the to-be-tested weighted image. A cumulative variance contribution may also be referred to as a variance cumulative contribution, and all of the foregoing are referred to as the cumulative variance contribution.

In some embodiments, the present disclosure provides a method for intelligent plan optimization, including a method for predicting a dose based on a distance feature and a method for automatic plan optimization based on the predicted dose. The method for predicting the dose based on the distance feature may including the following steps:

Obtaining the CT image, the contour image, and the dose data of a case, the contour image including the target region contour image and the OAR contour image.

Resampling the CT image, the contour image, and the dose data at the same resolution.

Obtaining, based on the target region contour image after resampling, the contour coordinates of the target region, calculating the shortest distance from the voxel coordinates of each OAR image to the contour coordinates of the target region after resampling, and constituting the distance image of the OAR.

Combining the distance image of the OAR and the corresponding resampled OAR contour image to form the weighted contour image based on distance weighting.

Performing a dimensionality reduction on all the weighted contour images, and expanding 3D contour images weighted by each OAR into the one-dimensional vectors, then performing the dimensionality reduction by the principal component analysis, converting this group of the one-dimensional vectors into the principal components through an orthogonal transformation, selecting the greatest principal components according to the variance so that the variance cumulative contribution reaches a set proportion, and restoring the one-dimensional vectors to the three-dimensional image to obtain the weighted contour image after the dimensionality reduction;

Performing regression training on the resampled CT image, the resampled target region contour image, the weighted contour image after the dimensionality reduction and the corresponding dose data by using a 3D-Unet model to obtain the trained regression model.

Inputting the to-be-tested CT image, the target region contour image, and the weighted contour image after the dimensionality reduction into the trained regression model to obtain the dose prediction results.

In some embodiments, the CT image, the contour image, and the dose data may be resampled at the same resolution. First, the CT image may be resampled; then the dose data may be inserted into a Z-axis position where a CT slice is located by interpolation; then the dose data may be resampled and the resampled dose data may be filled to CT size using 0; then the contour image may be resampled and a non-contoured position may be filled with zero slices; and finally all 3D data may be cropped to a fixed size.

In some embodiments, the equation for calculating the shortest distance between the voxel coordinate of each OAR image and the contour coordinates of the target region after resampling may be:

$$D = \left( \min_{t \in V_{OARS}, s \in \Pi_{PTV}} d(t_{i,j,k}, s)_{i,j,k} \right)_{l \times h \times w};$$

where D denotes the shortest distance, $V_{OARS}$ and $\Pi_{PTV}$ respectively denotes a set of 3D coordinates of the organ at risk and a set of 3D coordinates of the target region contour, t denotes a coordinate of a voxel at (i, j, k) in the organ at risk, s denotes a coordinate of a point on the target region contour, d denotes a distance function, and (l, h, w) denotes a count of slices, a length and a width of the distance image, respectively.

In some embodiments, combining the distance image of the OAR and the corresponding resampled OAR contour image to form the weighted contour image based on distance weighting may include:

taking a reciprocal of the distance image and then perform an inter-element multiplication with the corresponding contour image to form the weighted contour image based on the distance weighting, and the equation for the weighted contour image may be:

$$C' = \left(c_{i,j,k} * d'_{i,j,k}\right)_{l \times h \times w};$$

$$c_{i,j,k} = \begin{cases} 1, & c_{i,j,k} \in R_{OAR} \\ 0, & \text{others} \end{cases};$$

$$d'_{i,j,k} = \begin{cases} d^{-1}_{i,j,k}, & d_{i,j,k} \neq 0 \\ N, & d_{i,j,k} = 0 \end{cases};$$

where, C' denotes the weighted image, $c_{i,j,k}$ denotes a mask value of the voxel at (i, j, k) in the sample organ at risk image, which takes value of 0 or 1, $R_{OAR}$ denotes a set of 3D coordinates of a contoured region with a mask value of 1, d' denotes the reciprocal image, and N denotes a constant.

In some embodiments, before the regression training using the 3D-Unet model, the method may further include:

Converting the resampled dose data from numerical descriptions to classification descriptions, training the binary classification model to determine the classification results of each voxel, and filter the data in the region with dose as the input data for the regression training.

In some embodiments, performing regression training using the 3D-Unet model may include: the 3D-Unet model used may be a "U"-shaped structure, which includes 4 down-sampling operations and 4 up-sampling operations.

When the training is performed, each down sampling may include convolution, BN and RELU operation, each up sampling may include the splicing operation, and the training may be performed using an Adam optimizer with an early-stopping training method, so that when the loss on a revalidation set within a certain count of steps no longer decreases, the training may stop, so as to save the model parameters with the smallest loss on the validation set, i.e., obtain the trained regression model.

In some embodiments, based on the method for predicting the dose as described above, after obtaining the dose prediction results, the target function of the target region and the OAR may be calculated based on the dose prediction results, so as to complete the automatic plan optimization, and the target function equation may be:

$$F_{obj} = \sum_j \alpha_j * (d_j - p_j)^2;$$

where $d_j$ denotes a calculated dose at the jth point, $p_j$ denotes a dose value at the jth point in the dose prediction result, and $\alpha_j$ denotes a constraint penalty factor; the calculated dose $d_j$ corresponding to each point in the dose prediction result may be obtained by calculating a minimal value of the target function $F_{obj}$; a target radiotherapy plan may be obtained by optimizing $d_j$.

In some embodiments, the present disclosure may provide a system for predicting the dose based on the distance feature and a system for automatic plan optimization based on the predicted dose. The system for predicting the dose based on the distance feature may include the following modules.

An input module configured to obtain the CT image, the contour image and the dose data of the case.

A feature processing module configured to obtain the contour coordinates of the target region after resampling, calculate the shortest distance from the voxel coordinates of each OAR image after resampling to the contour coordinates of the target region to constitute the distance image at the same resolution, and combine the distance image of the OAR and the corresponding resampled OAR contour image to form the weighted contour image based on distance weighting, and then perform the dimensionality reduction to all the weighted contour images, expand the weighted 3D contour image of each OAR into the one-dimensional vector, then perform the dimensionality reduction using the principal component analysis, and select the principal components according to the variance cumulative contribution and reduce to the 3D image, to obtain the weighted contour image after the dimensionality reduction.

A training module configured to perform the regression training on the resampled CT image, the resampled target region contour image, the weighted contour image after the dimensionality reduction, and the corresponding dose data by using a 3D-Unet model, to obtain the trained regression model.

A prediction module configured to input the to-be-tested CT image, the target region contour image, and the weighted contour image after the dimensionality reduction obtained into the trained regression model to obtain the dose prediction result.

In some embodiments, the above-described system for predicting the dose may further include an optimization module. The optimization module may be configured to calculate the target function of the target region and the OAR according to the dose prediction result after the dose prediction result has been obtained to complete the automatic plan optimization, and the target function equation may be as follows:

$$F_{obj} = \sum_j \alpha_j * (d_j - p_j)^2;$$

where $d_j$ denotes a calculated dose at the jth point, $p_j$ denotes a dose value at the jth point in the dose prediction result, and $\alpha_j$ denotes a constraint penalty factor. The dose $d_j$ for each point in the dose prediction result may be obtained by calculating a minimal value of the target function $F_{obj}$, and a target radiotherapy plan may be obtained by optimizing an original radiotherapy plan based on the calculated dose $d_j$.

Figure 6:
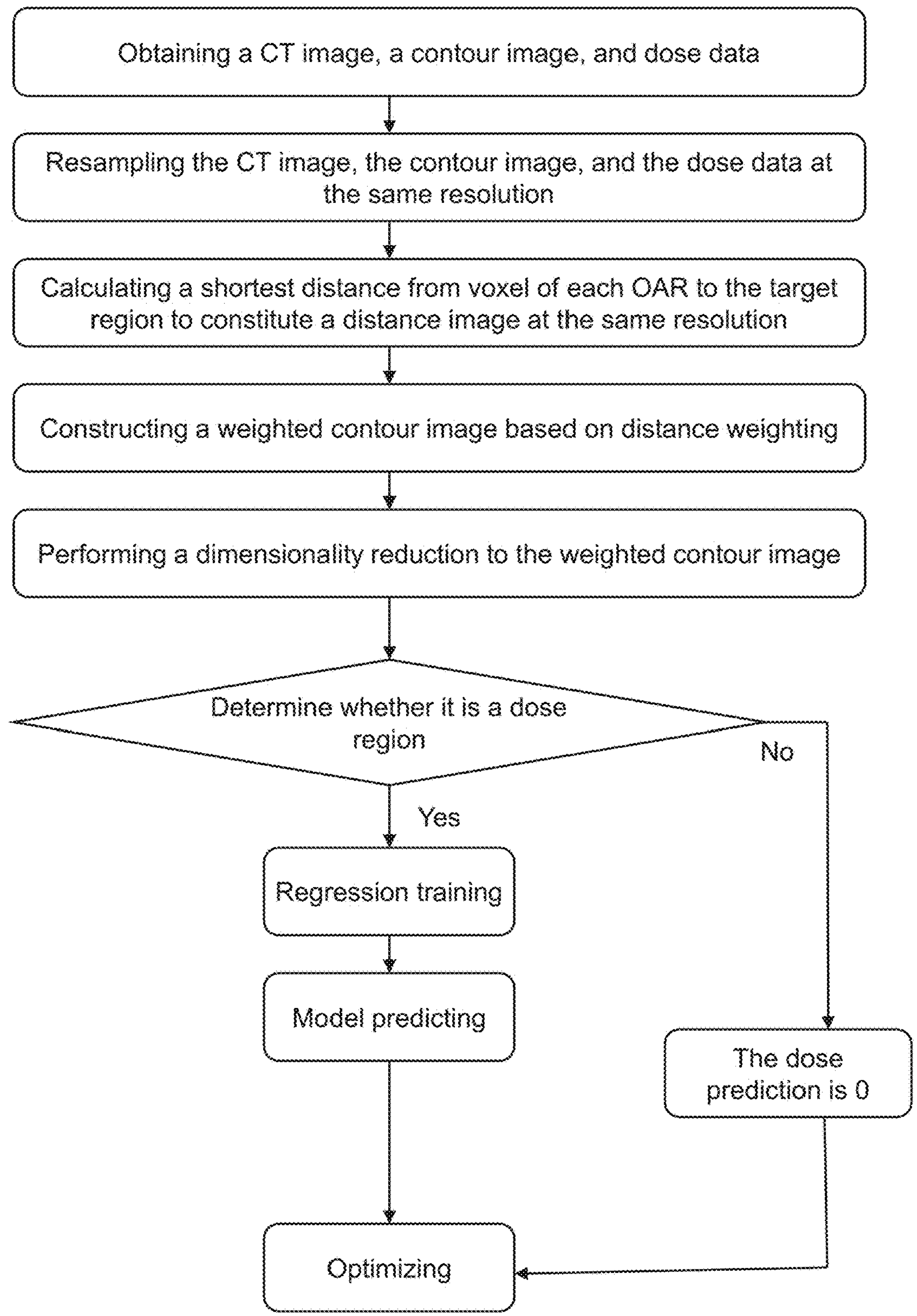
FIG. 6 is a flowchart illustrating another exemplary method for intelligent plan optimization according to some embodiments of the present disclosure.

FIG. 6 is a flowchart illustrating another exemplary method for intelligent plan optimization according to some embodiments of the present disclosure.

In some embodiments, as shown in FIG. 6, the method for intelligent plan optimization may include steps S1-S6:

S1, obtaining case data, including a CT image, one or more contour images, and dose data.

S2, performing a feature processing on the obtained data, and the steps of the feature processing may be as follows:

resampling the CT image, the contour image, and the dose data at the same resolution (e.g., 2.5 mm×2.5 mm×2.5 mm): resampling the CT image; inserting the dose data into a Z-axis position where a CT slice is located by means of interpolation; resampling the dose data, fill the resampled dose data to the size of the CT image by zero slices; resampling the contour image, with no contour positions filled with the zero slices; cropping all 3D data to a fixed size (e.g., 128×128×128).

Obtaining contour coordinates of the target region, calculating a shortest distance from voxel coordinates of each OAR to the contour coordinates of the target region to constitute distance images at the same resolution, and the equation for calculating the shortest distance may be:

$$D=\left(\min_{t\in V_{OARS},s\in\Pi_{PTV}} d(t_{i,j,k},s)_{i,j,k}\right)_{l\times h\times w};$$

where $V_{OARS}$ and $\Pi_{PTV}$ denote a set of 3D coordinates of the OAR and a set of 3D coordinates of a target region contour, respectively, t denotes the coordinates of the voxel at (i, j, k) in the OAR, s denotes the coordinates of a point on the target region contour, d denotes a distance function, and (l, h, w) denotes a count of slices, a length and a width of the distance image, respectively.

S3, combining the distance image of the OAR and the corresponding OAR contour image to form a weighted contour image based on distance weighting.

In some embodiments, the combining may include taking a reciprocal of each element of the distance image, and then performing an inter-element multiplication with the contour image. In some embodiments, the taking of the reciprocal may be as follows: if a value of the element in the distance image is non-zero, i.e., the coordinates are located within the contour, in other positions in a non-contoured and non-targeting region, and in the target region, the reciprocal of the element may be taken directly; if the value of the element is zero, that is, the coordinates are located on the target region contour, the reciprocal of the element may be a great value N. When taking the reciprocal of the element outside the contour and perform the inter-element multiplication with the element within the contour image, all of them may become zero, and the weighting may only be performed for the data within the contour, the equation may be as follows:

$$C'=\left(c_{i,j,k}*d'_{i,j,k}\right)_{l\times h\times w};$$

$$c_{i,j,k}=\begin{cases}1, & c_{i,j,k}\in R_{OAR}\\ 0, & \text{others}\end{cases};$$

-continued $$d'_{i,j,k}=\begin{cases}d_{i,j,k}^{-1}, & d_{i,j,k}\neq 0\\ N, & d_{i,j,k}=0\end{cases}$$

where C' denotes the weighted contour image, $c_{i,j,k}$ denotes a mask value of the OAR contour image, which takes value of either 0 or 1, $R_{OAR}$ denotes the contoured region with the mask value of 1, and d' denotes the reciprocal image, and N denotes a constant.

S4, performing the dimensionality reduction on all the weighted contour images, including: expanding each weighted contour image of the OAR weighted into the one-dimensional vector, performing the dimensionality reduction using principal component analysis, converting the group of the one-dimensional vectors of possible correlations into a group of linearly uncorrelated vectors based on an orthogonal transformation, which is served as principal components; descending an order of each of the principal component according to the variance, selecting a few of the principal components with the greatest variance whose variance cumulative contribution reaches a certain percentage (e.g., more than 95%) as target principal components; restoring, based on the target principal components, the one-dimensional vector to the 3D image to obtain the weighted contour image after the dimensionality reduction;

S5, performing model training and prediction on an initial 3D-Unet model based on the data after feature processing, the steps may include:

Dividing the case data into a training set, a validation set and a test set. Performing the regression training to the CT images, the target region contour images, the weighted contour images after the dimensionality reduction, and the corresponding dose data of the training set by using the 3D-Unet model. The 3D-Unet model may be a "U"-shaped structure, including 4 down-sampling operations and 4 up-sampling operations. The details are as follows: 1. Pytorch may be used to construct the 3D-Unet model, and an input image size of the 3D-Unet model may be 6×128×128×128, 6 denotes a count of channels; 2. The 3D-Unet model may include two convolutional layers connected sequentially. A convolutional kernel size may be 3, a filling may be 1, and a step size may be 1 by default. The convolution operation of each convolutional layer may be followed by BN and RELU operations, and a first sub-feature image may be output. The first sub-feature image may have a size of 16×128×128×128; 3. The first image may be input into a pooling layer to perform down-sampling operations, the same convolution operation may be performed twice sequentially on the output of the pooling layer to output the first feature image. A size of the first feature image may be 32×64×64×64; 4. The operation of step 3 may be repeated for three times based on the first feature image to output a fourth feature image. A size of the fourth feature image may be 256×8×8×8; 5. An up-sampling operation may be performed based on the fourth feature image using a transpose convolution with a convolution kernel of 2 and a step size of 2. The output of the up-sampling operation may be spliced with the input before the last down sampling to obtain a fifth spliced image. A size of the fifth spliced image may be 256×16×16×16. The same convolution operation may be sequentially performed on the fifth spliced image for twice to output the fifth feature image, and a size of the fifth feature image may be 128×16×16×16; 6. The operations of step 5 may be repeated for three times based on the fifth feature image to output an eighth feature image. A size of the eighth feature image may be 16×128×128×128; 7. The eighth feature image may be input into the convolutional layer with a convolutional kernel of 1 and an output channel of 1, and the corresponding image may be output, which has a size of 1×128×128×128, and is corresponding to the prediction of the dose. The Adam optimizer may be used to set a learning rate to 3e-4, a weight decay to 1e-4. An early-stopping training method may be used to stop training when the loss on the revalidation set is no longer decreasing for a certain count of steps. The model parameters with the smallest loss on the validation set may be saved, i.e., the trained regression model may be obtained. Due to the dimensionality reduction of the data, the data dimensionality may be reduced, and a difficulty of training may be subsequently reduced.

S6, inputting the CT images, the target region contour images, and the weighted contour images obtained after the dimensionality reduction of the test set into the trained regression model to obtain the dose prediction results. The obtaining of the distance image may be equivalent to taking a feature extraction, and then the combination with the contour image may be equivalent to a feature transformation of the contour. Such kind of artificially designed features may be a common operation in machine learning, which is also used in deep learning to improve the prediction accuracy.

After obtaining the dose prediction result, the method may also include the automatic plan optimization, including the calculation of the target functions for the target region and the OAR. The target function F is given by the following equation:

$$F_{obj} = \sum_j \alpha_j * (d_j - p_j)^2$$

where, $d_j$ denotes the calculated dose at the jth point, which is calculated based on a radiation field intensity, $p_j$ denotes the predicted dose at the jth point, and $\alpha_j$ denotes a constraint penalty factor. For the OAR, when $d_j > p_j$, the jth point may violate the constraint, and $\alpha_j$ may be a non-zero factor; when $d_j < p_j$, the jth point may satisfy the constraint, and $\alpha_j$ may be 0. For the target region PTV, when $d_j < p_j$, the jth point may violate the constraint, and $\alpha_j$ may be the non-zero factor; when $d_j > p_j$, the jth point may satisfy the constraint, and $\alpha_j$ may be 0. The minimal value of the target function $F_{obj}$ may be calculated to obtain the calculated dose $d_j$ at each point, and the plan may be obtained by $d_j$ optimization.

As an embodiment, considering a presence of a great count of no dose regions in the resampling of the dose data, before the regression training using the 3D-Unet model, the dose prediction method may further include:

Converting the dose data from a numerical description to a classification description, with no dose region denoted by 0 and dose region denoted by 1; training a binary classification model to determine a classification result of each voxel, and to screen the region with the prediction result of 1, i.e., the dose region, for the regression training. The specific approach may be performing an inter-element multiplication operation between the mask data about whether there is a dose or not obtained by classification, and the dose data output by the regression model, and then preforming the loss with the real dose data. The classification model and the regression model may have the same input data. In this way, a training volume of the model may be reduced, and the training efficiency may be improved.

One or more embodiments of the present disclosure may further provide a device for intelligent plan optimization including a processor. The processor may be configured to perform the method for intelligent plan optimization as described in any of the preceding embodiments.

One or more embodiments of the present disclosure may further provide a computer-readable storage medium storing computer instructions. When the computer reads the computer instructions in the storage medium, the computer runs the method for intelligent plan as described in any of the above embodiment.

The basic concepts have been described above, and it is obvious to those skilled in the art that the above detailed disclosure serves only as an example and does not constitute a limitation of the present disclosure. While not expressly stated herein, various modifications, improvements, and amendments may be made to the present disclosure by those skilled in the art. Those types of modifications, improvements, and amendments are suggested in the present disclosure, so those types of modifications, improvements, and amendments remain within the spirit and scope of the exemplary embodiments of the present disclosure.

Also, the disclosure uses specific words to describe embodiments of the disclosure, such as "an embodiment," "one embodiment," and/or "some embodiment" means a feature, structure, or characteristic associated with at least one embodiment of the present disclosure. Accordingly, it should be emphasized and noted that two or more references in the present disclosure, at different positions, to "one embodiment" or "an embodiment" or "an alternative embodiment" in different places in the present disclosure do not necessarily refer to the same embodiment. In addition, certain features, structures, or characteristics in one or more embodiments of the present disclosure may be suitably combined.

Additionally, unless expressly stated in the claims, the order of the processing elements and sequences, the use of numerical letters, or the use of other names as described in the present disclosure are not intended to qualify the order of the processes and methods of the present disclosure. While some embodiments of the invention that are currently considered useful are discussed in the foregoing disclosure by way of various examples, it is to be understood that such details serve only illustrative purposes, and that additional claims are not limited to the disclosed embodiments, rather, the claims are intended to cover all amendments and equivalent combinations that are consistent with the substance and scope of the embodiments of the present disclosure. For example, although the implementation of various components described above are embodied in a hardware device, it may also be implemented as a software only solution, e.g., an installation on an existing server or mobile device.

Similarly, it should be noted that in order to simplify the presentation of the application of the present disclosure, and thereby aiding in the understanding of one or more embodiments of the present disclosure, the foregoing descriptions of embodiments of the disclosure sometimes combine a plurality of features into a single embodiment, accompanying drawings, or descriptions thereof. However, this manner of disclosure does not imply that the objects of the present disclosure require more features than those mentioned in the claims. Rather, claimed object matter may lie in less than all features of a single foregoing disclosed embodiment.

Some embodiments use counts to describe counts of the components and attributes, and it may be understood that such counts used in the description of the embodiments are modified in some examples by the modifiers "about,"

"approximately," or "substantially." Unless otherwise noted, the terms "about," "approximately," or "substantially" indicates that a ±20% variation in the stated count is allowed. Correspondingly, in some embodiments, the numerical parameters used in the disclosure and claims are approximations, which change depending on the desired features of individual embodiments. In some embodiments, the numerical parameters should take into account the specified count of valid digits and employ general place-keeping. While the numerical domains and parameters configured to confirm the breadth of their ranges in some embodiments of the present disclosure are approximations, in specific embodiments, such values are set to be as precise as practicable.

For each of the patents, patent applications, patent application disclosures, and other materials cited in the present disclosure, such as articles, books, disclosure sheets, publications, documents, etc., the entire contents of which are hereby incorporated herein by reference. Application history documents that are inconsistent with or conflict with the contents of the present disclosure are excluded, as are documents (currently or hereafter appended to the present disclosure) that limit the broadest scope of the claims of the present disclosure. It should be noted that in the event of any inconsistency or conflict between the descriptions, definitions, and/or use of terms in the materials appended to the present disclosure and those set forth herein, the descriptions, definitions and/or use of terms in the present disclosure shall prevail.

Finally, it should be understood that the embodiments described in the present disclosure are only configured to illustrate the principles of the embodiments of the present disclosure. Other deformations may also fall within the scope of the present disclosure. As such, alternative configurations of embodiments of the present disclosure may be viewed as consistent with the teachings of the present disclosure as an example, not as a limitation. Correspondingly, the embodiments of the present disclosure are not limited to the embodiments expressly presented and described herein.

What is claimed is:

1. A method for intelligent plan optimization, comprising a method for predicting a dose based on a distance feature and a method for automatic plan optimization based on a predicted dose, wherein the method for predicting a dose based on a distance feature includes:

obtaining a computed tomography (CT) image, one or more contour images, and dose data of a case, wherein the one or more contour images include at least one contour image of a target region and at least one contour image of an organ at risk (OAR);

resampling the CT image, the one or more contour images, and the dose data at a same resolution;

obtaining contour coordinates of the target region, and calculating a shortest distance from each voxel coordinate of the OAR to the contour coordinates of the target region to obtain a distance image of the OAR, wherein the shortest distance from each voxel coordinate of the OAR to the contour coordinates of the target region is determined by a following equation:

$$D = \left( \min_{t \in V_{OARS}, s \in \Pi_{PTV}} d(t_{i,j,k}, s)_{i,j,k} \right)_{l \times h \times w};$$

where $V_{OARS}$ and $\Pi_{PTV}$ respectively denote a set of 3D coordinates of the OAR and a set of 3D coordinates of a contour of the target region, $t_{i,j,k}$ denotes a coordinate of a voxel at (i, j, k) in the OAR, s denotes a coordinate of a point on the contour of the target region, d denotes a distance function, and l, h, w denote a count of slices, a length, and a width of the distance image, respectively;

obtaining a weighted contour image based on distance weighting by combining the distance image and the at least one contour image of the OAR, including:

obtaining a reciprocal image by taking a reciprocal of the distance image;

obtaining the weighted contour image based on distance weighting by inter-element multiplication based on the reciprocal image and the at least one contour image, the inter-element multiplication being performed by following equations:

$$C' = (c_{i,j,k} * d'_{i,j,k})_{l \times h \times w};$$

$$c_{i,j,k} = \begin{cases} 1, & c_{i,j,k} \in R_{OAR} \\ 0, & \text{others} \end{cases};$$

$$d'_{i,j,k} = \begin{cases} d^{-1}_{i,j,k}, & d_{i,j,k} \neq 0 \\ N, & d_{i,j,k} = 0 \end{cases};$$

where, C' denotes the weighted contour image, $c_{i,j,k}$ denotes a contour mask value, which takes value of 0 or 1, $R_{OAR}$ denotes a contoured region with a mask value of 1, $d'_{i,j,k}$ denotes an inverse distance from a voxel at (i, j, k) in the OAR, and N denotes a constant;

performing a dimensionality reduction on all weighted contour images, expanding each weighted three-dimensional (3D) contour image of the OAR into an one-dimensional vector, performing the dimensionality reduction using principal component analysis, converting a group of one-dimensional vectors into principal components based on an orthogonal transformation; selecting, according to variance, a plurality of principal components with a greatest variance such that a variance cumulative contribution reaches a certain percentage; restoring the one-dimensional vector to a 3D image to obtain a weighted contour image after the dimensionality reduction;

obtaining a trained regression model by performing a regression training using a 3D-Unet model based on the CT image, the at least one contour image of the target region, the weighted contour image after the dimensionality reduction, and the dose data; and obtaining a dose prediction result by inputting a to-be-tested CT image, a to-be-tested contour image of the target region, and a to-be-tested weighted image after the dimensionality reduction into the trained regression model.

2. The method for predicting a dose based on a distance feature of claim 1, wherein the resampling the CT image, the one or more contour images, and the dose data at a same resolution includes:

resampling the CT image;

inserting the dose data by means of interpolation to a position on a Z-axis at which a CT slice is located;

resampling the dose data and filling resampled dose data to a size of the CT image using zeros;

resampling the one or more contour images and filling zero slices at a non-contoured position; and cropping all 3D data to a fixed size.

3. The method for predicting a dose based on a distance feature of claim 1, wherein before performing the regression training using the 3D-Unet model, the method for predicting a dose based on a distance feature further includes:
converting the dose data from numerical descriptions to classification descriptions, training a binary classification model to determine a classification result of each voxel, and screening data from a region with dose as input data for the regression training.

4. The method for predicting a dose based on a distance feature of claim 1, wherein the 3D-Unet model used may be a "U"-shaped structure, and performing the regression training using the 3D-Unet model includes 4 down-sampling operations and 4 up-sampling operations;
during training, each down sampling includes convolution, batch normalization (BN) and rectified linear unit (RELU) operations, each up sampling includes a splicing operation, and the training is performed using an Adam optimizer with an early-stopping training method, when a loss on a revalidation set within a certain count of steps no longer decreases, the training stops, model parameters with a smallest loss on the validation set are saved to obtain the trained regression model.

5. The method for intelligent plan optimization of claim 1, wherein the regression training includes:
training, based on training samples, a discriminant network and a regression model using a generative adversarial network.

6. The method for intelligent plan optimization of claim 5, wherein the regression training further includes:
determining, based on a tumor type, different training samples and labels corresponding to the different training samples; and
alternately training the regression model based on the different training samples of different scale sizes, wherein the different training samples have different learning rates during a training process, and the learning rates are adjusted based on a training sample feature.

7. The method for intelligent plan optimization of claim 5, wherein the learning rates include learning rates of a plurality of training stages, a learning rate of each of the plurality of training stages being updated based on a training loss of the training stage.

8. The method for automatic plan optimization based on a predicted dose of claim 1, wherein according to the method for predicting a dose based on a distance feature of claim 1, after the dose prediction result is obtained, a target function for the target region and the OAR is determined based on the dose prediction result to complete an automatic plan optimization, the target function being as follows:

$$F_{obj} = \sum_j \alpha_j * (d_j - p_j)^2$$

where $d_j$ denotes a calculated dose at a jth point, $p_j$ denotes a predicted dose at the jth point, and $\alpha_j$ denotes a constraint penalty factor;
the calculated dose $d_j$ corresponding to each point is determined by calculating a minimal value of the target function $F_{obj}$; and
a plan is obtained by optimizing based on the calculated dose $d_j$ corresponding to each point.

9. The method for predicting a dose based on a distance feature of claim 1, wherein a resolution of the to-be-tested CT image is determined based on a tumor type, a tumor position, and a tumor size corresponding to the to-be-tested CT image.

10. The method for predicting a dose based on a distance feature of claim 9, wherein the resolution is determined by:
determining a resolution interval based on the tumor type, the tumor position, and the tumor size;
generating a plurality of candidate resolutions based on the resolution interval; and
determining a target resolution based on the plurality of candidate resolutions.

11. The method for predicting a dose based on a distance feature of claim 10, wherein the determining a target resolution based on the plurality of candidate resolutions includes:
for each of the candidate resolutions,
obtaining a candidate CT image, a candidate contour image of the target region, and a candidate weighted contour image corresponding to the candidate resolution by resampling based on the candidate resolution;
determining, based on the candidate CT image, the candidate contour image of the target region, and a downscaled candidate weighted contour image, a candidate dose prediction result corresponding to the candidate resolution by the regression model;
determining an optimized resolution based on the candidate resolution and the candidate dose prediction result corresponding to the candidate resolution; and
determining the target resolution based on the optimized resolution.

12. The method for predicting a dose based on a distance feature of claim 1, wherein a target principal component is determined based on the to-be-tested contour image and a cumulative variance contribution.

13. The method for predicting a dose based on a distance feature of claim 12, wherein the target principal component is determined based on the to-be-tested CT image, the to-be-tested contour image, and the cumulative variance contribution using a principal component determination model, the principal component determination model being a machine learning model.

14. A system for intelligent plan optimization, comprising a system for predicting a dose based on a distance feature and a system for automatic plan optimization based on a predicted dose, wherein the system for predicting a dose based on a distance feature includes:
an input module configured to obtain a computed tomography (CT) image, one or more contour images, and dose data of a case;
a feature processing module, configured to:
after resampling, obtain contour coordinates of a target region, and calculate a shortest distance from each voxel coordinate of an organ at risk (OAR) to the contour coordinates of the target region to obtain a distance image at a same resolution, wherein the shortest distance from each voxel coordinate of the OAR to the contour coordinates of the target region is determined by a following equation:

$$F_{obj} = \sum_j \alpha_j * (d_j - p_j)^2;$$

where $V_{OARS}$ and $\Pi_{PTV}$ respectively denote a set of 3D coordinates of the OAR and a set of 3D coordinates of a contour of the target region, $t_{i,j,k}$ denotes a coordinate of a voxel at (i, j, k) in the OAR, s denotes a coordinate of a point on the contour of the target region, d denotes a distance function, and l, h, w denote a count of slices, a length, and a width of the distance image, respectively;

obtain a weighted contour image based on distance weighting by combining the distance image and at least one contour image of the OAR, including:

obtaining a reciprocal image by taking a reciprocal of the distance image;

obtaining the weighted contour image based on distance weighting by inter-element multiplication based on the reciprocal image and the at least one contour image, the inter-element multiplication being performed by following equations:

$$C' = \left(c_{i,j,k} * d'_{i,j,k}\right)_{l\times h\times w};$$

$$c_{i,j,k} = \begin{cases} 1, & c_{i,j,k} \in R_{OAR} \\ 0, & \text{others} \end{cases};$$

$$d'_{i,j,k} = \begin{cases} d_{i,j,k}^{-1}, & d_{i,j,k} \neq 0 \\ N, & d_{i,j,k} = 0 \end{cases};$$

where, C' denotes the weighted contour image, $c_{i,j,k}$ denotes a contour mask value, which takes value of 0 or 1, $R_{OAR}$ denotes a contoured region with a mask value of 1, $d'_{i,j,k}$ denotes an inverse distance from a voxel at (i, j, k) in the OAR, and N denotes a constant;

perform a dimensionality reduction on all weighted contour images, expand each weighted three-dimensional (3D) contour image of the OAR into an one-dimensional vector, perform the dimensionality reduction using principal component analysis, convert a group of one-dimensional vectors into principal components based on an orthogonal transformation; select, according to variance, a plurality of principal components with a greatest variance such that a variance cumulative contribution reaches a certain percentage; restore the one-dimensional vector to a 3D image to obtain a weighted contour image after the dimensionality reduction;

a training module configured to obtain a trained regression model by performing a regression training using a 3D-Unet model based on the CT image, at least one contour image of the target region, the weighted contour image after the dimensionality reduction, and the dose data; and a prediction module configured to obtain a dose prediction result by inputting a to-be-tested CT image, a to-be-tested contour image of the target region, and a to-be-tested weighted image after the dimensionality reduction into the trained regression model.

15. A system for automatic plan optimization based on a predicted dose, comprising the system for predicting a dose based on a distance feature of claim 14, wherein the system for automatic plan optimization based on a predicted dose further comprises an optimization module configured to:

after the dose prediction result is obtained, determine a target function for the target region and the OAR based on the dose prediction result to complete an automatic plan optimization, the target function being as follows:

$$F_{obj} = \sum_j \alpha_j * (d_j - p_j)^2$$

where $d_j$ denotes a calculated dose at a jth point, $p_j$ denotes a predicted dose at the jth point, and $\alpha_j$ denotes a constraint penalty factor;

determine the calculated dose $d_j$ corresponding to each point by calculating a minimal value of the target function $F_{obj}$; and obtain a plan by optimizing based on the calculated dose $d_j$ corresponding to each point.

* * * * *